(12) United States Patent
Wang et al.

(10) Patent No.: US 8,088,415 B2
(45) Date of Patent: Jan. 3, 2012

(54) DIFFUSION-CONTROLLED DOSAGE FORM AND METHOD OF FABRICATION INCLUDING THREE DIMENSIONAL PRINTING

(75) Inventors: Chen-Chao Wang, West Windsor, NJ (US); Jaedeok Yoo, East Windsor, NJ (US); Esteban Bornancini, North Wales, PA (US); Willie J. Roach, Plainsboro, NJ (US); Monica Rewachand Motwani, Somerset, NJ (US)

(73) Assignee: The Massachusetts Institute of Technology, Cambridge, MA (US)

( * ) Notice: Subject to any disclaimer, the term of this patent is extended or adjusted under 35 U.S.C. 154(b) by 1683 days.

(21) Appl. No.: 10/431,353

(22) Filed: May 6, 2003

(65) Prior Publication Data
US 2004/0005360 A1 Jan. 8, 2004

Related U.S. Application Data

(60) Provisional application No. 60/378,449, filed on May 6, 2002, provisional application No. 60/425,094, filed on Nov. 8, 2002.

(51) Int. Cl.
*A61K 9/50* (2006.01)
(52) U.S. Cl. .................. 424/497; 424/468; 424/482
(58) Field of Classification Search .................. 424/468, 424/482, 497
See application file for complete search history.

(56) References Cited

U.S. PATENT DOCUMENTS

| | | | | |
|---|---|---|---|---|
| 4,524,060 A | * | 6/1985 | Mughal et al. | 424/459 |
| 4,716,041 A | * | 12/1987 | Kjornaes et al. | 424/468 |
| 4,810,502 A | * | 3/1989 | Ayer et al. | 424/473 |
| 5,133,974 A | * | 7/1992 | Paradissis et al. | 424/480 |
| 5,204,055 A | | 4/1993 | Sachs et al. | 419/2 |
| 5,490,882 A | | 2/1996 | Sachs et al. | 134/1 |
| 5,490,962 A | | 2/1996 | Cima et al. | 264/22 |
| 5,593,697 A | * | 1/1997 | Barr et al. | 424/490 |
| 5,775,402 A | | 7/1998 | Sachs et al. | 164/4.1 |
| 5,934,343 A | | 8/1999 | Gaylo et al. | 141/12 |
| 6,213,168 B1 | | 4/2001 | Gaylo et al. | 141/12 |
| 6,238,704 B1 | * | 5/2001 | Suzuki et al. | 424/497 |
| 6,280,771 B1 | | 8/2001 | Monkhouse et al. | 424/484 |
| 6,336,480 B2 | | 1/2002 | Gaylo et al. | 141/12 |
| 6,471,992 B1 | | 10/2002 | Yoo et al. | 424/484 |
| 6,485,746 B1 | * | 11/2002 | Campbell et al. | 424/468 |
| 6,547,994 B1 | | 4/2003 | Monkhouse et al. | 264/40.1 |
| 2001/0038852 A1 | | 11/2001 | Kolter et al. | |
| 2002/0015728 A1 | * | 2/2002 | Payumo et al. | 424/451 |
| 2005/0015728 A1 | * | 1/2005 | Ragan et al. | 715/765 |

FOREIGN PATENT DOCUMENTS

| | | |
|---|---|---|
| WO | WO 00/29202 | 5/2000 |
| WO | WO 00/29202 A | 5/2000 |
| WO | WO 01/87272 A | 11/2001 |
| WO | WO01/87272 A2 | 11/2001 |
| WO | WO 01/87272 A2 | 11/2001 |

OTHER PUBLICATIONS

Wang, Chen-Chao, "Application of Polymers in CAD/CAM Processing of Pharmaceutical Products," Oct. 29, 2000, pp. 1-68.
Wang, Chen-Chao et al., "A Novel Approach for Fabrication of Toxic Anticancer Oral Dosage Forms," Oct. 29, 2000, pp. 1-20.
Wang, Chen-Chao et al., "Application of a Novel Solid Free-Form Fabrication Technology in Controlled-Release Oral Dosage Forms," Oct. 29, 2000, pp. 1-22.
U.S. Appl. No. 09/482,970, filed Jan. 12, 2000, Gaylo et al.
U.S. Appl. No. 09/861,480, filed May 18, 2001, Payumo.
U.S. Appl. No. 09/904,190, filed Jul. 10, 2001, Rowe.
U.S. Appl. No. 10/284,039, filed Oct. 29, 2002, Pryce Lewis et al.
U.S. Appl. No. 10/284,425, filed Oct. 29, 2002, Teung et al.
U.S. Appl. No. 10/284,430, filed Oct. 29, 2002, Pryce Lewis et al.
U.S. Appl. No. 10/366,868, filed Feb. 13, 2003, Monkhouse et al.
U.S. Appl. No. 60/487,447, filed Jul. 14, 2003, West et al.
Katstra et al., "Oral dosage forms fabricated by Three Dimensional Printing," *Journal of Controlled Release*, 66(1):1-9, 2000.
Rowe et al., "Multimechanism oral dosage forms fabricated by three dimensional printing," *Journal of Controlled Release*, 66(1):11-17, 2000.
Katstra W E et al: "Oral dosage forms fabricated by Three Dimensional Printing" Journal of Controlled Release, Elsevier Science Publishers B.V., Amsterdam, NL, vol. 66, No. 1, May 2000, pp. 1-9.
Rowe C W et al: "Multimechanism oral dosage forms fabricated by three dimensional printing" Journal of Controlled Release, Elsevier Science Publishers B.V., Amsterdamn, NL, vol. 66, No. 1, May 2000, pp. 11-17.
Deng-Guang Yu, et al., Novel Drug Delivery Devices for Providing Linear Release Profiles Fabricated by 3DP; International Journal of Pharmaceutics (2009), vol. 370, 160-166.
Yourong Fu, et al., Fast-melting Tablets based on highly plastic granules; Journal of Controlled Release (2005), vol. 109, 203-210.
Deng-Guang Yu, et al., A novel fast disintegrating tablet fabricated by three-dimensional printing; Drug Development and Industrial Pharmacy (2009), iFirst, 1-7.

* cited by examiner

*Primary Examiner* — Michael G Hartley
*Assistant Examiner* — Micah-Paul Young
(74) *Attorney, Agent, or Firm* — Rick Matos; Innovar, L.L.C.

(57) ABSTRACT

The invention includes a core-and-shell dosage form or unit in which the core contains API and in which the shell substantially governs the release such as by controlling diffusion of API through the shell. The shell may comprise a release-blocking polymer, and particles of a release-regulating polymer. The shell may be substantially impervious but the release-regulating polymer may become suitable to allow diffusion through it when activated. The core may include a buffer region between the shell and the API-containing portion of the core. The dosage form may include multiple units. The dosage form of the invention is capable of providing a release profile whose time scale can be adjusted by adjusting powder composition, and which may be approximately zero-order release. The invention further includes methods of manufacturing such a dosage form, such as three-dimensional printing.

62 Claims, 12 Drawing Sheets

Stage 1   Stage 2   Stage 3   Final Product

Line to Line Spacing (μm)

| DDS | 200 | 250 | 300 | 350 | 400 | 450 | 500 | 550 | 600 |
|-----|-----|-----|-----|-----|-----|-----|-----|-----|-----|
| 300 |     |     |     | Good | Good | Good | Fair | Fair | Poor |
| 400 |     |     | Good | Good | Good | Fair | Poor | Poor |      |
| 500 |     | Good | Good | Fair | Fair | Poor | Poor |      |      |
| 600 | Good | Fair | Fair | Poor | Poor | Poor |      |      |      |

| Good | Fair | Poor |
|------|------|------|

*FIG. 6*

Nominal 16 hour release

Immediate release Sudafed

DIFFUSION-CONTROLLED DOSAGE FORM AND METHOD OF FABRICATION INCLUDING THREE DIMENSIONAL PRINTING

BACKGROUND OF THE INVENTION

1. Field of the Invention

This invention relates generally to a diffusion-controlled dosage form and more particularly to a three-dimensionally printed polymer containing shell dosage form allowing diffusion controlled release of an Active Pharmaceutical Ingredient.

2. Description of the Related Art

There are at least two physical mechanisms that can be important in controlled release drug delivery, namely erosion and diffusion. Erosion involves the physical removal of both Active Pharmaceutical Ingredient (API) and excipient from a dosage form, such as by dissolution in bodily fluids or by degradation by bodily fluids. In an erosion-dominated dosage form, at the conclusion of release, the dosage form essentially no longer exists as an intact solid unit.

The other physical mechanism which is sometimes used in controlled release drug delivery is diffusion. Diffusion involves the passage of API out of the dosage form, while the non-API material of the dosage form substantially remains in the dosage form. Diffusion is governed by concentration gradients and diffusivities. At the end of release of API from a diffusion-controlled dosage form, the dosage form has approximately the same overall dimensions as it did at the time of administration to the patient, but the API has passed out of the dosage form by diffusion. Such a dosage form may pass completely through the digestive tract of the patient retaining approximately its original dimensions. As an example of diffusion-controlled dosage forms, oral dosage forms have been fabricated with an API-containing interior and a coating which has been a release barrier. The release barrier has been permeable to water and digestive fluids, while not being soluble in these liquids. Ingestion of the dosage form by the patient has resulted in water diffusing through the release barrier and beginning to dissolve the API inside the dosage form. The dissolved API has then diffused outward through the release barrier into the patient's digestive system. The release barrier has typically been a single substance which has had a desired permeability for water or aqueous solutions of interest and typically has had a thickness of less than approximately 50 micrometers. Diffusion-controlled release has usually required that the release barrier be substantially free of macroscopic defects. A variation of this, which is a release barrier having microporosity, has been created by depositing, onto the surface of a pre-manufactured tablet, a coating containing both an insoluble substance and micronized sugar. The sugar eventually dissolved out leaving a micro-porous membrane that controlled diffusion of the contents of the interior of the dosage form.

There have also been dosage forms that comprise a diffusion barrier that covers some but not all of the surfaces of the dosage form. In such a dosage form, the barrier has not completely controlled diffusion.

Another controlled release dosage form involving diffusion has been a device known as an osmotic pump. Such devices have been constructed from a core containing the API, a selectively impermeable coating with a defined exit orifice, and a hygroscopic salt or other material which has swelled when wet and has squeezed the API out through the orifice.

Up until the present time, manufacturing diffusion-controlled dosage forms has involved multiple manufacturing processes, one process to manufacture the interior, and another process to apply a coating or release barrier that controls the release. For example, applying the release barrier has been performed by creating a liquid layer around the outside of an already-formed dosage form, and allowing the liquid to dry, or by fluidized bed methods or by pan-coating. This has involved a multi-step manufacturing sequence including two significantly different types of manufacturing processes and typically using different raw materials for each of the manufacturing processes. In the case of the osmotic pump, in addition to the multi-step manufacturing process already described and the need for the film to be defect free other than at the defined exit orifice, this type of dosage form has suffered from the need for an exact size orifice.

FIGS. 1A and 1B illustrate the three-dimensional printing process. Three-dimensional printing (3DP) has sometimes been used to make dosage forms. The ability of 3DP to deposit specific quantities and compositions of material in specific places has provided the ability to design and manufacture dosage forms in a detailed way which has not been achievable with other dosage form manufacturing techniques. Three-dimensional printing has, for example, been used to make a dosage form with a core-and-shell geometry as disclosed in Pending U.S. application Ser. No. 09/861,480, entitled "Method and form of a drug delivery device such as encasing a hazardous core within a pharmacologically inert substance in an oral dosage form." Core-and-shell dosage forms have also been described in "Application of Polymers in CAD/CAM Processing of Pharmaceutical Products," AAPS, October 2000. These disclosures do not solve the problems of the present invention. For example, the AAPS disclosure used a shell to control diffusion, however, the shell was not perforation-free and it did not have the ability to closely and repeatably control the release profile.

Porosity has existed in many 3DP printed parts in most industries, but the existence of porosity has often been considered a disadvantage, because for many purposes solid parts have really been what have been desired. For dosage forms, porosity may be useful. However, for diffusion-controlled dosage forms, porosity would only be useful if it could be closely controlled. In order to use 3DP to make a diffusion-controlled dosage form, one choice would be that the shell would have to be made with a controlled porosity in order to achieve a desired diffusivity, which has been difficult. The other choice would be that the shell would have to be made essentially free of macroscopic defects and porosity, and then a controlled amount of porosity or diffusivity would have to be introduced or created. Making the defect-free shell by 3DP has not been achieved, either. Until the present invention, it simply has not been possible to make a dosage form shell by three-dimensional printing that is sufficiently continuous (solid) to be a part of accurately controlling the release by diffusion from a dosage form. More particularly, it has been difficult to make a sufficiently solid shell while leaving other portions of the article porous. Thus, until now, the possibility of single-process manufacturing and the ability for precise design of a dosage form, both of which might be achieved by 3DP, have been essentially unavailable for making diffusion-controlled dosage forms.

For a dosage form governed by diffusion, the natural release profile is that the cumulative amount of API released is proportional to the square root of time since initiation of release, i.e., $Q=k*t^{0.5}$. The release rate of such a dosage form is the derivative of this function, namely: $r=k'*t^{-0.5}$, which is a release rate that decreases with time. However, for many API, a desirable release profile would be to release API in approximately a constant release rate, which is a zero-order release. In most cases, diffusion-controlled dosage forms have not provided release profiles that are sufficiently close to a zero-order release profile.

Accordingly, it would be desirable to be able to make diffusion-controlled dosage forms by a single-process manufacturing scheme, i.e., to make both the core and the shell approximately simultaneously by a single process. It would be desirable to provide a powder-based manufacturing process that uses only a single powder and yet can achieve shell properties that are different from the core properties. It would be desirable to make a three-dimensionally printed dosage form which comprises a substantially solid, non-porous shell even while other portions of the dosage form have porosity. It would be desirable to provide a three-dimensionally printed dosage form that contains a shell capable of accurately controlling the release of API by diffusion through the shell. It would be desirable for a manufacturing process to permit adjustment of the time scale of the release profile of a dosage form by a simple adjustment of the composition of powder that is used in the manufacturing process. It would also be desirable to provide a nearly zero-order release profile from a diffusion-controlled dosage form. Diffusion-controlled dosage forms of the type described would be especially useful for API that are highly water-soluble, which have been difficult to release in a controlled manner. It would be desirable to provide appropriate manufacturing processes to achieve all of these things.

BRIEF SUMMARY OF THE INVENTION

The invention includes a core-and-shell unit or dosage form in which the core contains API and in which the shell substantially governs the release such as by controlling diffusion of API through the shell. The shell may comprise a release-blocking polymer together with a release-regulating polymer interspersed within the release-blocking polymer. The shell may also comprise a plasticizer mixed in with the release-blocking polymer. The shell may be essentially continuous and free of leak paths when it is dry, but may have a known diffusivity when it is wet with aqueous liquids. The core may include a buffer region, which is free of API, between the shell and an API-containing central portion of the core. If desired, the dosage form may include multiple units that may be joined to each other and may be separated from each other under specified conditions. The dosage form of the invention is capable of providing a release profile that is close to zero-order. The invention permits adjustment of the time scale of the release profile by adjustment of proportions of the two types of polymers. The invention further includes methods of manufacturing such a dosage form, such as by three-dimensional printing, which is suitable for making the entire dosage form in one process.

BRIEF DESCRIPTION OF THE SEVERAL VIEWS OF THE DRAWING(S)

FIG. 6 illustrates combinations of drop-to-drop spacing and line-to-line spacing that give various qualities of binding and structural integrity in a ribbon test according to principles of the present invention.

DETAILED DESCRIPTION OF THE INVENTION

The present invention includes a core-and-shell construction of a diffusion controlled oral dosage form. The core contains an Active Pharmaceutical Ingredient (API) and the shell substantially governs the release of the API. The shell may contain a release-blocking polymer combined with a release-regulating polymer. The shell may further contain a plasticizer mixed in with the release-blocking polymer. The core may further include a buffer region between the shell and an API-containing core. Another aspect of the invention is that the dosage form may be manufactured in one process, for example, by three-dimensional printing (3DP). According to another embodiment of the invention, the dosage form may include multiple individual units that may be joined to each other and may be separated from each other under specific conditions. Another embodiment of the present invention is a dosage form having a zero order release profile.

Figure 2:
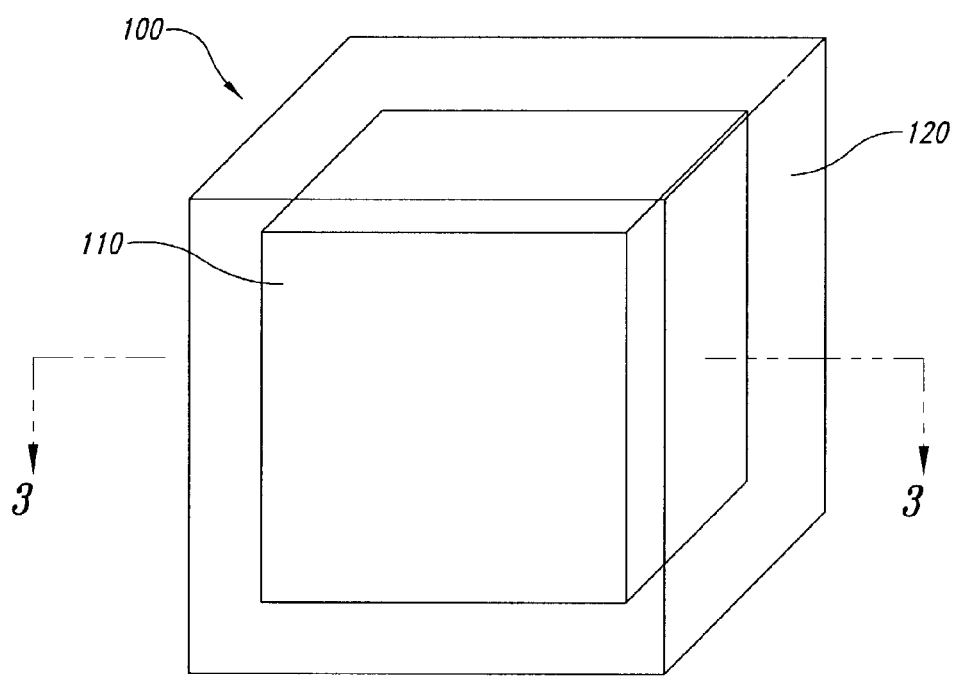
FIG. 2 illustrates an isometric view of the core and shell geometry of a unit or of a dosage form that comprises only one unit, shown as being of approximately cubical shape according to principles of the present invention.
Figure 3A:
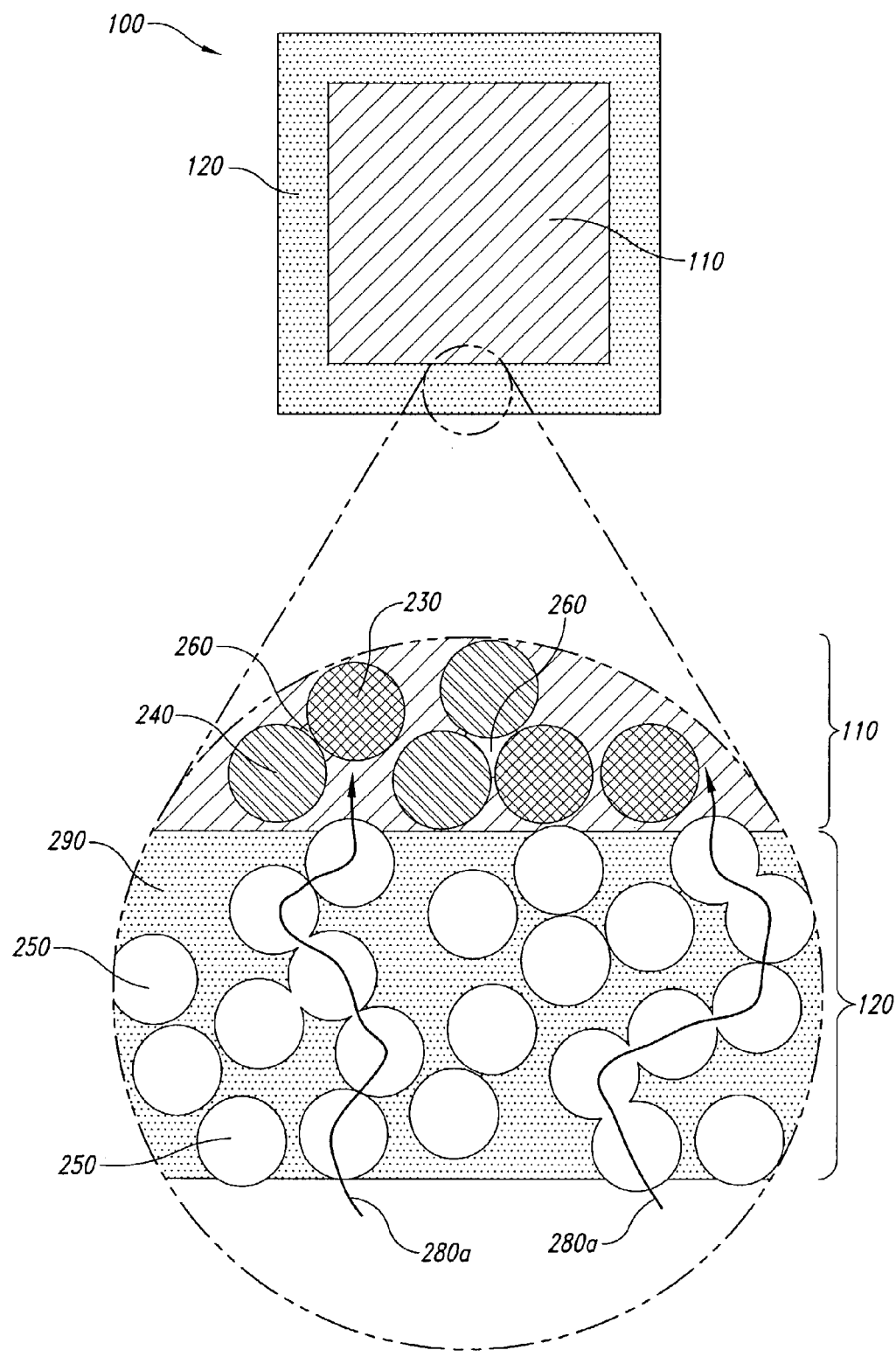
FIG. 3A is a cross-section of FIG. 2 that illustrates one embodiment of the present invention wherein the shell comprises a release-regulating polymer that exists in the form of identifiable particles according to principles of the present invention.
Figure 3B:
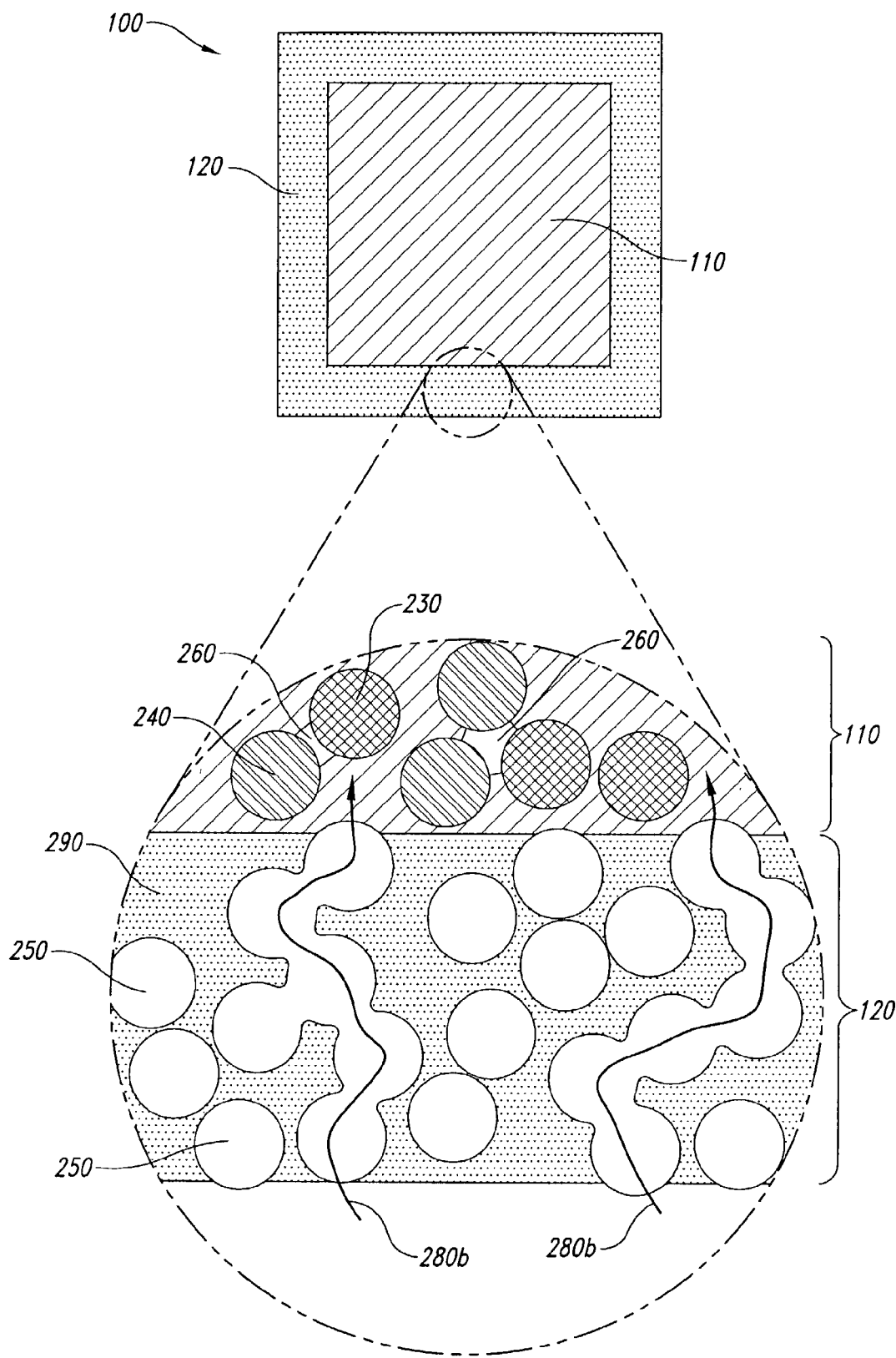
FIG. 3B illustrates the release-regulating polymer having the form of an interconnected network according to principles of the present invention.

As shown in FIG. 2, the present invention includes a dosage form that comprises at least one unit 100. The unit 100 may comprise a core 110 and a shell 120, in which the shell 120 completely surrounds the core 110. The exemplary dosage form illustrated in FIG. 2 is approximately cubical in shape. FIG. 3 is a cross-section of the dosage form shown in FIG. 2.

The core 110 may contain powder particles and may contain Active Pharmaceutical Ingredients (API). The amount of API contained in the core may be chosen according to the desired dose of API chosen for therapeutic effectiveness of a particular API. This amount may vary widely depending on the nature of the API.

The powder particles may comprise at least two different kinds of particles each having their own composition, with the particles being mixed together with each other, as described elsewhere herein. The powder particles in the core may comprise both particles 230 of a release-blocking polymer and particles 240 of a release-regulating polymer. It is possible that some or even all of the particles 230, 240 in the core 110 may not be bound to each other or to any other particle.

Alternatively, it is possible that at least some of particles 230 and 240 in the core 110 may be bound to each other at least to some degree. The binding may take the form of substances deposited between the powder particles 230, 240 that, as shown in FIG. 3, may at least partially occupy the space between the particles and may form necks 260 which connect either kind of powder particles 230, 240 to one or more adjacent particles 230, 240. The substance may be a core binder substance that binds particles together by surrounding or adhering to particles and partially occupying space between particles, although this is optional. The substance may be an API. The substance could be both a core binder substance and an API.

The core may have pores distributed throughout it, or may be substantially solid with very little porosity such as less than 5%. It is possible that some of the powder particles, such as the particles of the release-regulating polymer, may have API absorbed within them. It is possible that absorbed API within particles of release-regulating polymer may be the principal form in which API exists within the core. The API and optionally the core binder substance may be contained in substantially all of the core 110, or may be contained in less than all of the core 110, as described elsewhere herein in regard to the possible existence of a buffer region.

The API may be water-soluble, meaning that the API would be soluble in bodily fluids such as digestive fluids. For example, a highly water-soluble API may have solubility greater than 500 mg/cc at room temperature. However, it is not necessary that the API be soluble to that degree. A wide range of aqueous solubility of the API is possible. In any region such as the core or the portion of the core that contains API, there is an aggregate volume of space not occupied by powder particles, and this aggregate volume may be termed the void volume. For this void volume of the core, using known data for the solubility of the API in water, there is an amount of the API that could be dissolved in a volume of water equal to the void volume of the core at a specified temperature such as either room temperature or body temperature. In the present dosage form, the amount of API contained in the core could be less than or equal to the amount of API that than can be dissolved in the void volume of water.

Alternatively, the amount of API contained in the core could be greater than such amount. As described elsewhere herein, this choice can have an impact on the release profile of the API from the dosage form and on certain details of the manufacturing method used to manufacture the dosage form. The amount of API in the dosage form may be determined by the therapeutic dose for a particular API, which can vary widely. The dosage form described in the Examples uses a relatively high-dosage API, but other API could have lower amounts per unit of core volume.

The shell 120, which is shown in detail in FIG. 3(*a*) and FIG. 3(*b*), may surround the core 110 in all directions. The shell 120 may be constructed so that the shell regulates the passage of substances, including API, through the shell by diffusion. Accordingly, the shell 120 may be substantially continuous and substantially free of pinholes or macroscopic defects (on the order of two or three microns), at least at the time of administration of the dosage form to a patient. The shell 120 may comprise a composition that gives it desired diffusive properties when it is wet with water or aqueous solutions. The she 120 may contain no or substantially no API, may contain more API than the core, or any amount of API therebetween.

The shell may comprise a release-blocking polymer and a release-regulating polymer. One possible configuration of these substances to form a shell is shown in FIG. 3(*a*). The release-regulating polymer may exist in the shell 120 as identifiable particles which are release-regulating polymer particles 250 which by their touching may form paths such as 280*a*.

Alternatively, as shown in FIG. 3(*b*), the release-regulating polymer may exist in the shell 120 as tortuous paths 280*b* that may have narrower parts and wider parts. The release-regulating polymer could exist as a three-dimensionally interconnected network, whose appearance in cross-section would also be as shown in FIG. 3(*b*). The release-blocking polymer may exist as a substantially continuous phase 290 of the release-blocking polymer that either fully or partially incorporates the release-regulating polymer particles 250 or other form of the release-regulating polymer. The release-blocking polymer may surround, adhere to, or be in substantial contact with the release-regulating polymer particles 250 or other form of the release-regulating polymer, thereby incorporating the release-regulating polymer to form a continuous structure that is the shell 120.

If the release-regulating polymer exists in the shell as identifiable particles, the release-regulating polymer particles 250 in the shell may have overall dimensions which are somewhat less than the thickness of the shell 120, which contributes to the ability of the shell 120 to either partially or fully incorporate release-regulating polymer particles 250. The maximum external dimension of the release-regulating polymer particles 250 may, for example, be less than one-third of the thickness of the shell 120. In at least some instances, the release-regulating polymer particles 250 may touch each other or come in very close proximity to each other such that at least for some series of particles 250 there is a somewhat continuous path 280*a* from one side of the shell 120 to the other side, passing through various release-regulating polymer particles 250. Such a path 280*a* is labeled in FIG. 3(*a*).

Alternatively, as illustrated in FIG. 3(*b*), the release-regulating polymer may exist as a tortuous path 280*b* that may comprise narrower parts and wider parts. It is possible that the paths 280 may form a three-dimensionally interconnected network. Of course, any or all of these possible path geometries could exist together simultaneously in a shell 120.

The release-regulating polymer may be such that upon exposure to water, path 280 attains a state such that water and aqueous API solution can diffuse along that path through the shell 120. The release-regulating polymer may hydrate upon exposure to water. For example, the release-regulating polymer may be such that upon exposure to water or bodily fluids it forms a gel that permits diffusion through it of water and aqueous solutions. The release-regulating polymer may be such that its absorption of water is approximately independent of the pH of the water or aqueous solution to which it is exposed. The release-regulating polymer may be hydrophilic.

The other polymer present in the shell 120 is the release-blocking polymer. The release-blocking polymer may be present in the shell as a continuous phase 290. The release-blocking polymer may be substantially impermeable to water and to aqueous solutions and may be substantially insoluble in water. However, the release-blocking polymer may be soluble in other solvents. The release-blocking polymer may be soluble in solvents such as ethanol and other alcohols to an extent suitable to permit certain manufacturing processes as described elsewhere herein. The release-blocking polymer may be hydrophobic.

The release-blocking polymer by itself may have a glass transition temperature less than 50° C. Alternatively, the release-blocking polymer may be chosen such that in the presence of a plasticizer, the combination of release-regulating polymer and plasticizer has a glass transition temperature less than 50° C. Having such a transition temperature can be helpful in achieving a shell that is free of macroscopic defects. The release-blocking polymer may be chosen so that it is sufficiently pliable, either by itself or in the presence of a plasticizer, to undergo deformation in the form of a possible compressing operation, without suffering cracks.

The proportion of the release-blocking polymer and the release-regulating polymer in the shell may be chosen so as to achieve a desired time scale of the release profile of the unit or dosage form. For example, greater content of release-regulating polymer would generally result in a faster overall time scale of the release profile. In general, the release-blocking polymer may comprise at least 40% by volume of the shell, although this is only approximate.

The proportion of release-blocking polymer to release-regulating polymer in the shell may be substantially the same as the proportion of release-blocking polymer to release-regulating polymer in the core or may include any ratio designed to meet a given release profile.

The shell 120 may also comprise a plasticizer. More specifically, the release-blocking polymer in the shell may comprise a plasticizer. A plasticizer is a compound that may be added to a polymer to impart softness and flexibility, such as by causing polymer chains to relax. A plasticizer may be incorporated into a polymer to increase the workability, flexibility, or distensibility of a polymer by increasing the free volume between the polymer molecules. The increase in free volume increases the freedom of movement for molecules of the release-blocking polymer and therefore provides better fusing between particles of the release-blocking polymer to form a continuous phase 290 comprising release-blocking polymer.

A plasticizer may be a polymeric material and may be a low or moderate molecular weight liquid, or occasionally, a low melting point solid. A plasticizer may cause the glass transition temperature of a polymer to be lower than it would be in the absence of the plasticizer. The plasticizer may be present in the shell in any form. The plasticizer is not specifically shown in FIG. 3 because it might not exist in its own distinct regions and even if it did, these might be on a size scale that is far smaller than what is illustrated. The plasticizer may, for example, be present in the form of micelles or tiny drops interspersed in the release-blocking polymer. The plasticizer may be soluble in solvents such as ethanol or other alcohols.

The presence of a plasticizer compound in the release-blocking polymer may be helpful in achieving a shell which is free of cracks, macroscopic porosity, macroscopic defects, etc., because a material which includes a plasticizer would not be brittle and hence this would lessen the possibility of cracks forming in the shell due to brittleness. The need for a plasticizer may depend on how pliable the release-blocking polymer is in the absence of a plasticizer. A release-blocking polymer with a high glass transition temperature in the absence of a plasticizer may need a plasticizer, although a plasticizer could be used even if not considered necessary. A release-blocking polymer with a low glass transition temperature may not need a plasticizer.

The release-blocking polymer and the plasticizer and the concentration of the plasticizer (where it exists) may be chosen so as to result in the combination of the release-blocking polymer and the plasticizer having a desired glass transition temperature. They may be chosen so as to result in a glass transition temperature that is lower than a maximum allowable temperature to which the Active Pharmaceutical Ingredient (API) may be exposed without damage. The glass transition temperature of the combination of the release-blocking polymer and the plasticizer in the shell may be lower than the glass transition temperature of the release-blocking polymer in the core. The release-blocking polymer and a plasticizer and an appropriate concentration of plasticizer may be chosen so that the release-blocking polymer plus plasticizer is sufficiently pliable to undergo deformation in the form of a possible compressing operation, without suffering cracks.

The shell region may have a substantially uniform wall thickness (thickness perpendicular to its local surface) everywhere within a unit. Alternatively, the shell may be designed so that the shell wall thickness is not uniform everywhere within a unit. For example, in a unit having a rectangular prismatic shape there might be individual shell wall thicknesses in each of three different orthogonal directions. Within any given wall, the shell thickness might be uniform or might even be designed to be non-constant. In any case, it is still possible to practice the present invention. There may be constraints regarding achievable shell wall thicknesses, such as thicknesses being approximately a small integer multiple of a characteristic distance (drop-to-drop spacing, line-to-line spacing, or layer thickness) which is related to manufacturing, as discussed elsewhere herein. For various walls, the small integer multiple may be the same as or different from each other. The small integer may be as small as 2 or even 1. In general, the shell thickness in the present invention may be as small as 100 micrometers or smaller, or as large as 1000 micrometers or larger.

In regard to durability of polymer, there are at least two options concerning the materials and construction of the shell. One option is that the materials of the shell may be chosen and the shell may be manufactured so that the shell is substantially defect-free at the time of administration of the dosage form to a patient and, although the release-regulating polymer may become a gel upon exposure to aqueous liquids, the shell may remain substantially intact throughout the release. Another option is that the shell materials may be chosen and the shell may be manufactured so that the shell is substantially defect-free at the time of administration of the dosage form, but at least a component of the shell is suitable to degrade somewhat upon exposure to bodily fluids during time period of interest for controlled release. For example, the release-regulating polymer may be subject to degradation upon exposure to bodily fluids. The choice can depend on details of the desired release profile.

Figure 4:
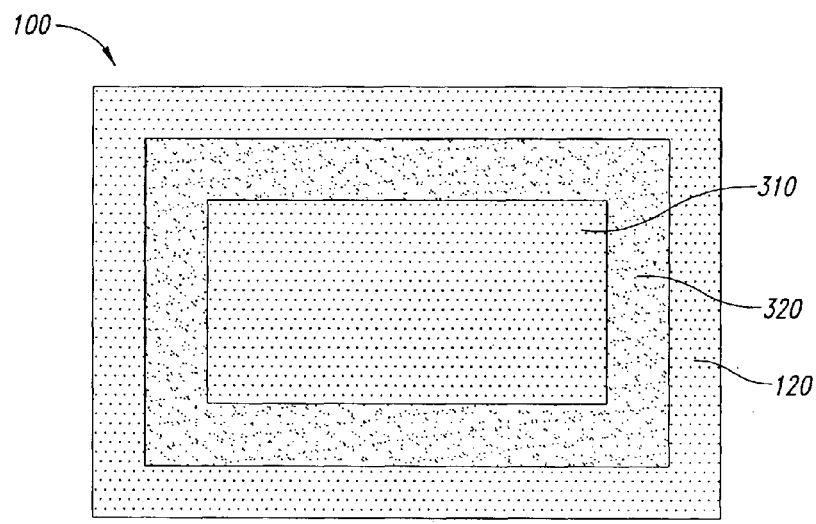
FIG. 4 illustrates a cross section of the dosage form of the present invention further including a buffer region between the core and the shell according to principles of the present invention.

As mentioned, the API-containing portion of the core may be less than the entire core. This is shown in FIG. 4, which is a cross-section of the unit or dosage form. For example, API may be contained in only a central portion 310 of the core 110. The invention may further include, within the core, a buffer region 320, located inside the shell 120 and separating the API-containing portion 310 of the core from the shell 120 in all or at least some directions. The buffer region 320 may completely surround the API-containing region 310. The buffer region 320 may contain powder particles but may be free of API and may optionally be free of any other binder substance. The powder particles in the buffer region may be unconnected to each other or they may be at least somewhat connected to each other such as by a non-API-containing substance. The powder particles in the buffer region may have substantially the same proportion of release-regulating polymer to release-blocking polymer as the rest of the core has. The buffer region may have dimensions which are chosen so as to help produce a desired delay time between the time of administration of the API to a patient and the time when any substantial amount of API begins to be released from the dosage form. Alternatively, it is possible that the buffer region may have dimensions that are chosen based on considerations related to bleeding, as described elsewhere herein.

It is possible that the buffer region or the entire core or any portion of the core may have void space between at least some of the powder particles. Alternatively, the buffer region or the entire core or any portion of the core may have powder particles and other substances in the core so packed together as to achieve a density having less than 5% void.

Figure 5:
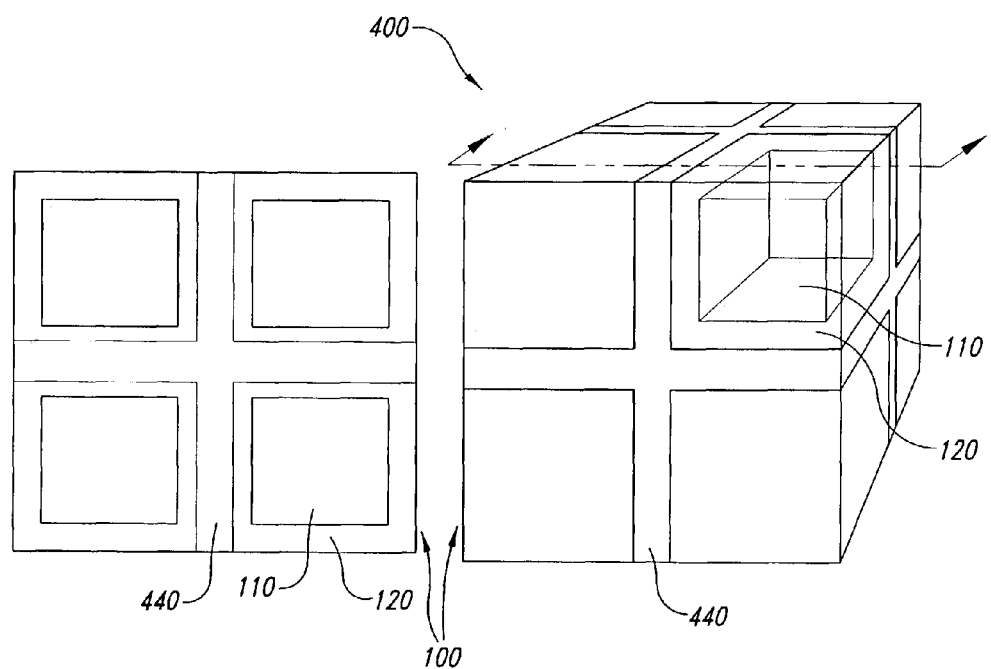
FIG. 5 illustrates a dosage form that comprises eight units joined to each other in an approximately cubical arrangement according to principles of the present invention.

The dosage form may consist of only one unit 100 having the core 110 and shell 120 designs that has already been described. Alternatively, as illustrated in FIG. 5, the dosage form may comprise more than one unit 100 which may be joined to one or more other units by inter-unit binding regions 440 to make up a dosage form 400. The inter-unit binding region 440 may comprise powder particles and an inter-unit binding substance. The powder particles in the inter-unit binding region may have substantially the same proportion of release-regulating polymer to release-blocking polymer as the core or the shell has. The inter-unit binding substance may be a substance suitable to cause the individual units 100 to separate from each other upon exposure to any aqueous liquid, or to cause the units to separate from each other upon exposure to a liquid of specified pH, such as the pH of gastric fluid or the pH of intestinal fluid.

If the dosage form comprises more than one unit 100, the individual units either may be identical to each other or may be different from each other. If the units are different from each other, the differences between units may be in any one or more of features of the units such as size, shape, the composition of the API contained within the units, quantity of API contained within the units, release characteristics of API from the units, etc. It is possible that not all of the units have the core-and-shell structure that has been described; it would for example be possible for some units to have a structure that does not have a shell, which would provide a more immediate release of API. It is possible for at least one unit to have a buffer region in its core while at least one other unit does not have a buffer region. Of course, it is also possible for different units to contain different API. FIG. 5 illustrates a dosage form 400 which comprises eight units 100 arranged in the form of two units by two units by two units in each of three mutually orthogonal directions, with each unit having at least approximately identical size and shape.

The dosage form as a whole or the individual unit or units may have a rectangular prismatic shape, which may be cubical. Other possible shapes include cylindrical and other shapes. The overall dimensions and shape of the dosage form, whether it is a single unit or multiple units, may be chosen for ease of swallowing by a patient.

It is possible that either one unit or multiple unconnected units or a built-up dosage form 400 comprising multiple units may be further enclosed by a capsule such as a gelatin capsule. A capsule may, for example, fit loosely around the units or dosage form. A gelatin capsule may, for example, improve ease of swallowing. It is possible that a plurality of units may simply be packaged together without being attached to each other, by being enclosed within a capsule.

Materials

The release-regulating powder particles may be or may include hydroxypropyl methylcellulose. Hydroxypropyl methylcellulose (HPMC) is a pharmaceutical excipient that forms a gel upon contact with water but degrades only very slowly. HPMC is hydrophilic. Other examples of possible release-regulating polymers are hydroxypropyl celluloses (HPCs); methylcelluloses or carboxymethyl celluloses; natural hydrogels such as xantham gum, locust bean gum, alginic acid derivatives, gellan gum, guar gum, tragacanth; vinyl pyrrolidone/vinyl acetate copolymers; and polyvinyl pyrrolidones.

The release-blocking polymer may be or may include Kollidon. Kollidon (BASF Corporation, Shreveport, La.) is a polymer that is useful in dosage forms, which comprises 80% polyvinyl acetate and 19% polyvinylpyrrolidone (the balance being, surfactant, stabilizer or other substances). It is soluble in ethanol. If this substance is used as the release-blocking polymer, a plasticizer might not be necessary, although a plasticizer could still be used. Another example of a possible release-blocking polymer is poly(ethyl acrylate, methyl methacrylate) trimethylammonioethyl methacrylate chloride, whose commercial name is Eudragit RSPO and Eudragit RLPO. Eudragit® RSPO is a pH independent polymer with low permeability for use in pharmaceutical formulations and is available from Rohm America (Degussa-Huls Corporation, Piscataway, N.J.). If Eudragit RSPO is used as the release-blocking polymer, it may require a plasticizer. Other examples of possible release-blocking polymers are polyvinyl acetate and ethyl celluloses.

An example of a plasticizer suitable for use with both Eudragit RSPO and Kollidon is triethyl citrate. Other examples of suitable plasticizers include triacetin, diethyl phthalate, acetyltriethyl citrate and acetyltributyl citrate. Still other examples of possible plasticizers include, but are not limited to, carboxylic acid esters and phosphoric acid esters. The plasticizer may be chosen to be sufficiently soluble in a selected solvent such as ethanol or another alcohol to permit the deposition of a sufficient amount of plasticizer to achieve the desired pliability or depression of the glass transition temperature of the release-blocking polymer.

The API may be at least somewhat water-soluble, which may be helpful for allowing API to diffuse out through the diffusion boundary after water has permeated through the diffusion boundary. The API may have, as a minimum aqueous solubility, a solubility that is related to the desired dose of API from the unit. As an example of a highly water-soluble API, the API may be chosen to have an aqueous solubility at room temperature that is greater than 500 mg/cc, which is the approximate solubility of pseudoephedrine hydrochloride, which is a highly water-soluble API. However, such a value of solubility is not required. Other possible API of interest includes metoprolol, d-chlorpheniramine maleate, chlorpheniramine maleate, diphenhydramine hydrochloride, caffeine, d-brompheniramine maleate, brompheniramine maleate, aminophylline, and orphenadrine citrate.

One substance that can be used as a viscosity modifier for liquids is polyvinyl pyrrolidone (ISP Technologies, New Milford, Conn.).

Method of Manufacture

One method of manufacturing the described dosage form is three-dimensional printing (3DP). 3DP provides the ability to precisely determine local geometric features and composition of a manufactured article, to an extent that is not possible with most other manufacturing methods.

Figure 1A:
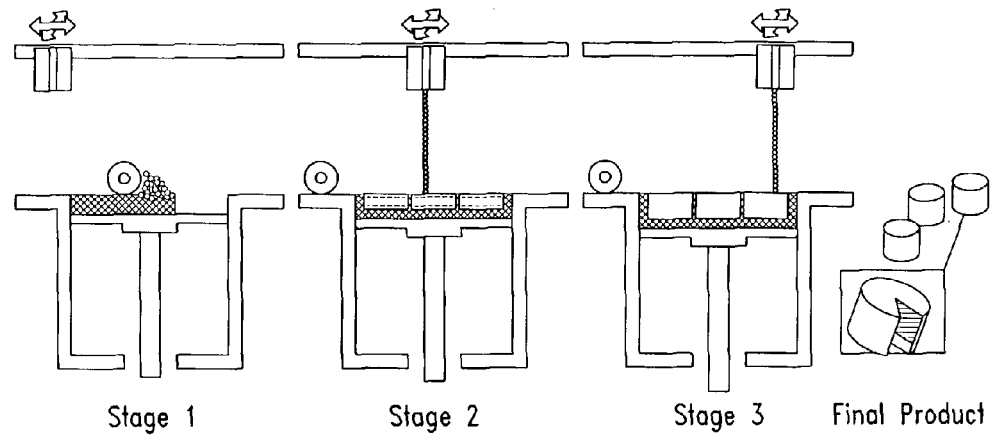
FIGS. 1A and 1B illustrate the three-dimensional printing process in accordance with prior art.
Figure 1B:
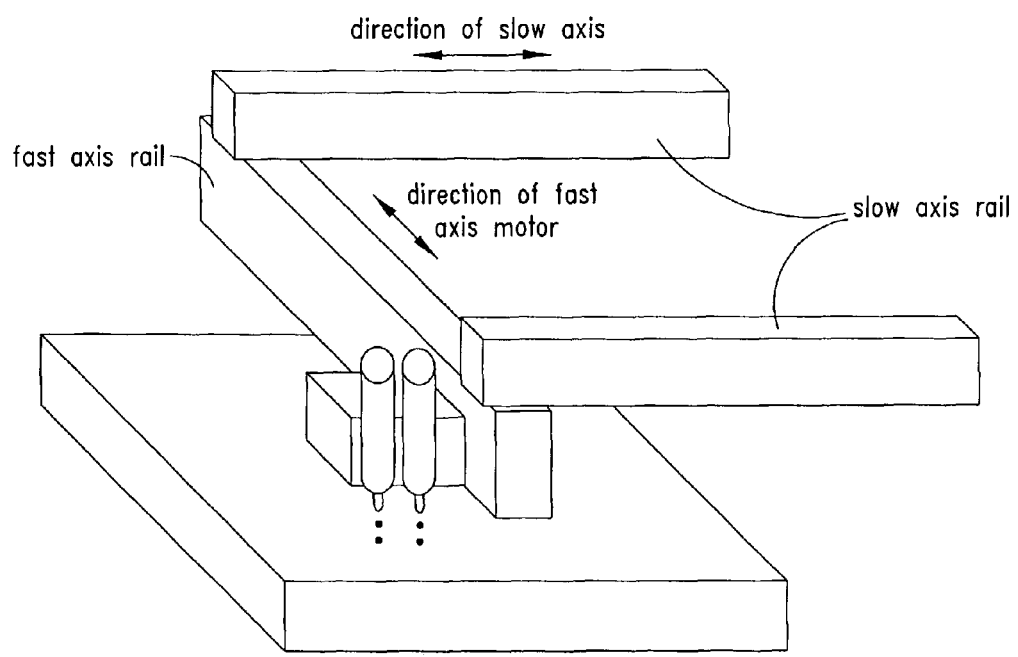

Three-dimensional printing, illustrated in FIG. 1, includes a set of steps which may be repeated as many times as are necessary to manufacture an article. At the beginning of the set of steps, powder may be deposited in the form of a layer. The powder may be deposited by roller spreading or by other means such as slurry deposition. Then, drops of a liquid may be deposited onto the powder layer to bind powder particles to each other and to other bound powder particles. At each powder layer, timing of drop deposition such as from a printhead may be coordinated, for example by software, with the motion of the printhead in two axes, to produce a desired pattern of deposited droplets.

For applications such as the present one, drops of a second liquid, and even if desired a third liquid, may also be dispensed in a appropriate patterns on the same powder layer. In such a situation, registration or coordination may be performed to accurately determine the relative placement of the various liquids. The term drops can be understood to include not only spherical drops but any of the various possible dispensed fluid shapes or structures as are known in the art. After this liquid dispensing process is completed on one layer, another layer of powder may be spread and the liquid dispensing may be repeated, and so on until a complete three-dimensional object has been built.

The printing pattern(s) in each printed layer may in general be different from the printing pattern(s) in other layers, with each printing pattern being chosen appropriately so as to form an appropriate portion of a desired object. The liquid may be dispensed by a dispensing device suitable for dispensing small quantities of liquid drops, which may resemble an ink-jet printhead. For example, the dispensing device could be a microvalve or it could be a piezoelectric drop-on-demand printhead or a continuous-jet printhead or other type of printhead as is known in the art.

During printing, the unbound powder supports the bound shape and the later deposited layers of powder. At the end of the printing process the unbound and untrapped powder may be removed, leaving only the shape that has been bound together. If desired for a specific purpose, heating may be performed either before or after unbound powder is removed.

In general, liquids that are dispensed onto the bulk material may be a pure liquid, or may include solid particles in the form of a suspension or may be a liquid containing solubilized Active Pharmaceutical Ingredient (API). One possible purpose of a dispensed liquid may be to deliver the API to the dosage form being manufactured, and such a liquid may be referred to as an API-containing liquid. Another possible purpose of the dispensed liquid may be to cause powder particles to bind to each other. Any of the dispensed liquids may serve either or both of these functions or some portion thereof.

Binding of the particles can occur through any of several mechanisms. One mechanism is that the dispensed liquid may be a solvent of at least some of the powder, in which case the dispensed liquid actually dissolves powder particles or portions of them. As the solvent in the dispensed liquid evaporates, the particles resolidify such that they are joined together. In this mechanism of binding, it is not necessary for the powder particles to dissolve completely; it is just necessary for enough dissolution to occur so that when the solvent substantially evaporates, the dissolved material together with any undissolved material forms a substantially solid mass.

Another mechanism is that the dispensed liquid may simply solidify around solid particles, thereby binding them. Yet another mechanism is that the dispensed liquid may contain a dissolved adhesive substance that is left behind when the volatile part of the dispensed liquid evaporates, thereby binding the particles together. The dissolved substance may be or include a binding substance. The dissolved substance may be an API. The dissolved substance may be or include a polymer. The dissolved substance may be or include a plasticizer.

The manufacturing method may comprise dispensing into the intended core region of the unit or dosage form an API-containing liquid. The API-containing liquid may simply serve as a means of placing the API within the dosage form, or it may also function as a binding agent. The API-containing liquid may be absorbed into at least some of the powder particles when it interacts with these particles.

The manufacturing method may comprise dispensing into the intended shell region of the unit or dosage form a shell binder liquid. The shell binder liquid may be free of the API that is dispensed into the core. As described elsewhere herein, the shell binder liquid may comprise a plasticizer and may be a solvent for the release-blocking polymer.

If a multi-unit dosage form is being manufactured, the manufacturing method may comprise dispensing into the intended inter-unit binding region of the unit or dosage form an inter-unit binder liquid, which may contain an inter-unit binding substance.

FIG. 1 illustrates a typical 3DP apparatus. The apparatus includes a printer including a first axis of movement, a second axis of movement that may be perpendicular to the first axis of movement, and a liquid dispensing device. The dispensing device can be moved with respect to a powder bed and can dispense drops of a liquid, or multiple liquids, onto a powder bed.

Three-dimensional printing can have spatial descriptors in each of three different, typically orthogonal directions. In three-dimensional printing, fluid may be deposited in drops or in fluid units resembling drops. Drops may be deposited in a succession that forms a line corresponding to the motion of the printhead. The spacing between those drops is the drop-to-drop spacing. After completion of one line, another line may be deposited adjacent to the earlier-deposited line and separated from the earlier-deposited line by a distance that is a line-to-line spacing. After completion of printing on a layer of powder, another powder layer may be deposited, with each powder layer having a layer thickness. The powder layer thickness is the third descriptor.

In three-dimensional printing, a voxel or unit volume may be defined by one drop-to-drop spacing in the fast axis direction of motion, by one line-to-line spacing in the slow axis direction of motion, and by one layer thickness in the vertical direction. Some of this unit volume is occupied by powder particles, and the remainder of the unit volume is empty space that collectively has a volume that is the void volume.

The saturation parameter describes how much of the void space in this unit volume is occupied by liquid which is dispensed in a drop or fluid unit which is dedicated to that particular voxel. The saturation parameter is the ratio of the dispensed fluid volume to the volume of empty space in the voxel. In general, in three-dimensional printing, saturation parameters may be chosen to be slightly less than, or somewhere approximately equal to, 1.0. Excessively small saturation parameters tend to result in poor structural integrity of a manufactured part. Excessively large saturations parameters tend to result in excessive bleeding of liquid beyond where the liquid was deposited. In the present application the saturation parameter may be chosen, in the case of the shell, based upon what results in a defect-free shell, and may exceed 1.0 if necessary.

In the present invention, the powder that is deposited to form a layer for use in 3DP may include both particles of the release-blocking polymer and particles of the release-regulating polymer. The powder may be substantially identical everywhere within a deposited layer. Everywhere in a powder layer the deposited powder may, for example, have substantially the same proportion between the two types (release-blocking and release-regulating) of polymers. This means that the composition of the spread powder may be the same for local regions that eventually become part of the shell as it is for local regions that eventually become part of the core and for local regions that eventually become part of the inter-unit-binding region (if an inter-unit binding region is present).

The proportion of the release-blocking particles and the release-regulating particles may be chosen so as to determine the overall time scale of the release profile of API from the dosage form. A larger proportion of release-regulating polymer will result in a faster overall time scale of the release profile. More detailed types of powder spreading, which may include deposition of different compositions of powder in different places, are described in commonly assigned U.S. Pat. Nos. 5,934,343; 6,213,168; and 6,336,480.

As has been described, the shell of the dosage form of the present invention may be formed by the dispensing of a shell binder liquid onto the layer of powder. The shell binder liquid may be selected so that the release-blocking polymer is sufficiently soluble in the shell binder liquid so that the shell may be formed by at-least-partial dissolution of the release-blocking polymer followed by resolidification. A typical solvent used in the shell binder liquid may be ethanol or other alcohols or a mixture comprising a substantial fraction of ethanol.

As explained, the use of some polymeric materials may involve the use of a plasticizer. The plasticizer may be contained in the shell binder liquid that is dispensed onto the powder in the intended locations of the shell. The plasticizer and the solvent in the shell binder liquid may be selected so that the solvent in the shell binder liquid is a solvent for the plasticizer, so that the plasticizer can be delivered to specified places in the dosage form which is being manufactured. The plasticizer and the solvent in the shell binder liquid may be selected so that the plasticizer is sufficiently soluble in the solvent which is included in the shell binder liquid so that sufficient plasticizer can be delivered to the release-blocking polymer to achieve the desired pliability of the release-blocking polymer in places at which the shell binder liquid is deposited. During the three-dimensional printing process, the shell binder liquid may dissolve at least portions of particles of release-blocking polymer and then when the solvent in the shell binder liquid evaporates, both release-blocking polymer and the plasticizer may come out of solution and may be left behind together when the solvent evaporates.

The shell binder liquid may also include a viscosity-modifying agent suitable to produce a desired viscosity of the shell binder liquid by virtue of the agent being dissolved in the shell binder liquid. Suitable thickening agents include polyvinyl pyrrolidone.

A typical shell binder formulation may be 15% by weight triethyl citrate (which is a plasticizer) dissolved in 85% by weight of a solvent which itself comprises water-ethanol in a 25:75 ratio (by weight). Ethanol and other organic solvents are known to have a relatively low surface tension such as approximately or less than 25 dyne/cm, which means that they can be more difficult to dispense in a precise, controlled manner than are liquids having a higher surface tension. In the practice of the present invention, the dispenser may be a microvalve, a piezoelectric drop-on-demand printhead, a continuous-jet-with-deflection printhead, or other type of dispenser or printhead as is known in the art. It has been found that, even if a liquid has a low surface tension, the liquid can be successfully and accurately dispensed by a microvalve with a flat-ended orifice, as long as it is realized that a puddle may exist at the end surface of the orifice on a somewhat continuous basis and as long as dispensing is performed without long interruptions. Techniques for such deposition are described in copending commonly assigned patent application U.S. Ser. No. 10/189,799, entitled "Apparatus, systems and methods for use in three-dimensional printing."

Another liquid that may be dispensed onto the powder layer during 3DP is an API-containing liquid intended to be deposited in the core 110 of the dosage form 100. The API-containing liquid may contain the API that is intended to be in the core of the unit. The API-containing liquid may further contain a binder substance, although this is optional. The API-containing liquid may further comprise a viscosity modifier and/or a surfactant, although these are optional. A possible API-containing liquid for deposition in the core is 50 wt % pseudoephedrine hydrochloride as an API, 5% polyvinyl pyrrolidone, 0.01% Tween 20 as a surfactant, and the balance water. The API pseudoephedrine hydrochloride is highly water-soluble. Other possible API, including other API that are highly water-soluble, are described elsewhere herein.

In some cases it may be desired to dispense into the core region an amount of API which can be contained in the amount of the API-containing liquid which can be deposited into the core region in one printing pass. In such case, the printing may comprise just one printing pass, followed by the spreading of the next layer of powder. In other cases, it may be desired to deposit into the core an amount of API Which is greater than the amount which can be deposited by one printing pass. In this case, it is possible to multi-pass print the core region, i.e., to dispense API-containing liquid in a first pass over the appropriate region of the powder bed, to allow that region to at least partially dry, to again dispense API-containing liquid into the same region, and so on, as many times as may be desired, followed by the spreading of the next layer of powder. This permits the deposition of larger amounts of API than could be deposited with a single pass.

Yet another liquid which may be dispensed onto the powder layer is an inter-unit binder liquid. The inter-unit binding liquid may contain the inter-unit binding substance. The inter-unit binding liquid may be free of API.

The choice of shell wall thicknesses (either for all of the shell walls or for shell walls on individual places within the dosage form) may be related to parameters that pertain specifically to the three-dimensional printing. Primitive features that can be printed by three-dimensional printing can include a layer (which may correspond to a deposited powder layer), a line (such as a pass along the fast axis direction of printing), and a drop.

The shell may be printed so that its thickness in one direction is formed by dispensing shell binder liquid into a small integer number of adjacent drops, and its thickness in another direction is formed by dispensing shell binder liquid into a small integer number of adjacent lines, and its thickness in another direction is formed by connecting a small integer number of adjacent layers. The small integers can in general be different from each other. It is possible that the powder layer thickness, the line-to-line spacing and the drop-to-drop spacing might not all be exactly equal to each other, which might mean that the three different shell thicknesses also would not exactly equal each other.

Alternatively, the powder layer thickness, the line-to-line spacing and the drop-to-drop spacing can be chosen to be substantially equal to each other. In general, the small integer can be different from place to place within the unit. The integer which describes the spacing in a particular direction as a multiple of a primitive feature dimension can be as small as, for example, 2. An absolute minimum value of the integer would be 1, and under some circumstances a value of 1 might be sufficient for producing a release barrier that is free of defects and pinholes. However, more confidence can be obtained with a value of 2. Still larger integers would provide even greater confidence, but would have an impact on the utilization of space inside the dosage form, because space that is utilized for the shell may be unavailable for placement of API.

It can be noted that the described process may produce, by three-dimensional printing, a shell that is substantially solid and continuous and free of pinholes, even while other parts of the dosage form, such as the core, may contain porosity. Producing a shell which is substantially solid and continuous and free of pinholes means that the diffusion through the shell, and hence the release of API from the dosage form, may be determined by the behavior and quantity of the particles of release-regulating polymer in the shell.

In ordinary 3DP, the product at the time of completion of 3DP frequently contains porosity, but in the dosage form of the present invention, in selected places (namely, the shell), there may be substantially no porosity, even while other parts of the dosage form (namely the core) may be porous. The substantially continuous shell may be achieved in part because of the use of a dispensed liquid that is a solvent for the release-blocking polymer, so that there is a process of at least partial dissolution of the particles of release-blocking polymer followed by resolidification.

The saturation parameter is the ratio of dispensed shell binder liquid assigned to a voxel, divided by the total amount of empty volume (void space) between powder particles in the voxel. Another factor which may help to achieve the substantially continuous shell is dispensing the shell binder liquid with a fairly large saturation parameter such as approximately or even slightly greater than 1.

A similar parameter that describes the amount of shell binder liquid dispensed is the volume of shell binder liquid in a drop compared to the overall volume of a voxel to which the drop is delivered. This parameter is more directly related to the conditions of operation of a three-dimensional printing machine in that it does not require knowledge of the actual packing fraction of particles. (A typical situation for powders is a packing fraction of approximately 50%, which means that the void fraction is 100%–50% or 50%, and so if the shell binder liquid is deposited at a volume of 0.50 milliliters of shell binder liquid per milliliter of overall voxel volume, for a powder packing fraction of 50%, the saturation parameter would be 1. For the same assumed powder packing fraction, a deposition of slightly more than 0.50 milliliters of shell binder liquid per milliliter of overall voxel volume would give a saturation parameter slightly more than 1.)

Yet another factor which may help to achieve the substantially continuous shell is dispensing shell binder liquid in a pattern such that in all directions the shell is at least two voxel units thick, i.e., at least two drop-to-drop spacings or two line-to-line spacings or two powder layer thicknesses. For single-voxel-thickness shells, producing reliably defect-free shells may require a larger a saturation parameter than is required for two-voxel-thickness shells.

Although this is optional, another factor helping to achieve the substantially continuous shell may be the use of a plasticizer in the shell binder liquid such that when the solvent in the shell binder liquid evaporates, the release-blocking polymer and the plasticizer solidify together and are closely mixed with each other. The plasticizer makes the polymer less brittle and more likely to heal defects.

It is further possible to heat the printed unit afterward to a temperature and for a time suitable to promote curing of the release-blocking polymer plus plasticizer. The heating may be done at a temperature which is suitable to cure the release-blocking polymer plus plasticizer, such as at a temperature above the glass transition temperature of that combination of substances, while (if desired) being below the temperature at which the API is thermally damaged and below the glass transition temperature of release-blocking polymer which does not contain plasticizer.

All of these techniques may be used together to achieve a shell that is substantially continuous, or some subset of less than all of these techniques, in any combination, may be used.

It is possible to print the dosage form such that there is a buffer region that may be formed by not dispensing upon certain space either the API-containing liquid or the shell binder liquid. This buffer region may be designed into the dosage form so that even with whatever bleeding of an individual deposited liquid might occur, the API-containing liquid deposited into the core would not meet the shell binder liquid, even as a result of bleeding of deposited liquids.

Alternatively, the buffer region may be designed to result in a desired delay characteristic in the release profile of API from the dosage form. The buffer region may be formed by not dispensing API-containing liquid or shell binder liquid into a small integer number of drop-to-drop spacings and line-to-line spacings and powder layer thicknesses in an appropriate pattern so as to surround the central region of the core in all directions and so as to in turn be surrounded in all directions by the shell.

Yet another possibility for the present invention may arise if it is desired that the dosage form comprise multiple units which are attached to each other at the time of administration of the dosage form but separate from each other after administration of the dosage form. Manufacture of such a dosage form may involve all of the previously described actions and also may involve dispensing yet a third liquid onto the powder bed in appropriate places. This third liquid may be termed the inter-unit binding liquid. Dispensing of this liquid may be suitably coordinated and registered with the dispensing of the shell binder liquid and the API-containing liquid. As described elsewhere herein, the inter-unit binder substance may be soluble in water or may be soluble only in aqueous solutions of a specified pH range.

One of the later steps in manufacturing by three-dimensional printing may be to heat the articles being manufactured. Heating may be performed to accelerate evaporation of volatile substances such as solvents. Heating may be performed to help make the shell more defect-free by heating the shell to a temperature at which it is somewhat soft, which may encourage possible defects in the shell to heal through a curing process. In particular, this can be done if the release-blocking polymer (together with plasticizer, if present) has a glass transition temperature which is less than a maximum allowable temperature to which the Active Pharmaceutical Ingredient may be exposed without damage, so that the dosage form may be heated to a temperature which is above the glass transition temperature of the release-blocking polymer (together with plasticizer, if present) but below the temperature for damage to the Active Pharmaceutical Ingredient.

If plasticizer is present, it is possible that heating may be performed at a temperature which is above the glass transition temperature of the release-blocking polymer containing plasticizer, i.e., the combination which is present in the shell, but is below the glass transition temperature of unplasticized release-blocking polymer which exists elsewhere in the dosage form such as in the core. In this way, curing of polymer and healing of possible defects may be caused to occur in the shell, while not occurring in the core. It is possible that a heating step can be used either for the purpose of drying or for the purpose of healing defects or for both of these purposes simultaneously. Heating may be performed either before or after the harvesting and de-dusting of the units, or both before and after the harvesting and de-dusting.

As yet another option, the manufacture of the dosage forms of the present invention can include compression of the dosage form after completion of three-dimensional printing. Compression can remove most of the inter-particle void space and can result in a large amount of deposited API being included within the final dimensions of a dosage form, which may, for example, be chosen based on a constraint such as ease of swallowing. For example, compression may be performed by placing a three dimensionally printed unit or dosage form in a die and compressing it with a ram as described in commonly assigned U.S. patent application Ser. No. 10/284,430.

For example, compression may be performed such as to result in a void fraction of less than 5% everywhere in the unit or dosage form. The appropriate choice of polymer or polymer plus plasticizer can enable the release barrier to be sufficiently flexible to survive the significant deformations occurring during the compression process without experiencing the creation of any new cracks, pinholes or defects.

How the Dosage Form Works Upon Being Administered to a Patient

If the dosage form comprises multiple units attached to each other, upon administration to a patient, the dosage form may break up into individual units either upon administration or later. For example, the dosage form may break up upon exposure to any liquid, or specifically to gastric fluid, or specifically to intestinal or other types of fluid, such as may be determined for example by the pH of the fluid.

Upon exposure to water or body fluids, the release-regulating polymer in the shell may absorb water or body fluids. Absorbing water or body fluids into the shell, which may be free of API, may require a certain period of time. This may help the unit or dosage form to avoid releasing any initial burst release of API, which is a sometimes undesirable phenomenon which has been known to occur with other types of dosage forms. The release-regulating polymer may, for example, become a gel upon absorbing water or body fluids. As a result, there may be formed paths through the shell that allow diffusion of liquids through it in either direction or both directions. Body fluids such as digestive fluids, or components of such fluids, may pass through the shell into the interior of the unit.

If the unit comprises a buffer region, such fluid may also have to pass through the buffer region after passing through the shell, before encountering API. The buffer region may be designed and sized so that it helps to provide a delay of initial release of API from the dosage form. (As described elsewhere herein, another factor that may be used in sizing the buffer region may be the extent of bleeding which occurs under specific printing conditions.) As described elsewhere herein, a delay time of several hours is achievable, if desired. The existence of a delay time may itself be desirable for a particular API. In addition, as described in connection with the use of multiple units in a dosage form, the existence of a delay time may be useful in obtaining a desired overall release profile for an entire dosage form as a combination of various release profiles of individual dosage forms.

When the fluid seeping into the core encounters API, the fluid may dissolve API to form an aqueous API-containing solution in the core region of the dosage form. The aqueous API-containing solution may then diffuse outward through the shell and thereby be released into the patient's digestive system.

As described elsewhere herein, in any region such as the core or the portion of the core that contains API, there is an aggregate volume of space not occupied by powder particles, which may be termed the void volume. For this void volume, together with known solubility data for a particular API, there is an amount of the API that could be dissolved in a volume of water equal to the void volume at a specified temperature such as either room temperature or body temperature. In the present dosage form, the amount of API contained in the core could be less than or equal to the amount of API that can be dissolved in the void volume of water. In this case, the concentration of API in the liquid inside the core may start out at its maximum value early in the time after fluid has diffused into the core, and may then decrease as time progresses and diffusion of API out of the core occurs.

Alternatively, it is possible that the amount of API in the core is more than what could be dissolved by the amount of water that can occupy the void spaces in the core. In this case, it is possible that when water or body fluid enters the core, the water or fluid creates inside the shell an aqueous solution of API having the saturation concentration of API, and some solid API will remain in the core. Then, as diffusion of API out of the core takes place, some of the undissolved API may further dissolve, and there may continue to be a saturated aqueous solution of API in the core region for some time until all of the remaining solid API has dissolved, so that for a portion of the release profile this aqueous solution may have an essentially constant API concentration as a source which drives the diffusion. This latter situation may help to attain a nearly zero-order release profile, at least for as long as there remains undissolved solid API in the core.

As described elsewhere herein, it is possible that as time progresses, there may be changes in or dissolution of or degradation of the release-regulating polymer in the shell, resulting in an increase in the diffusivity through the shell. Such a mechanism and design would help to accelerate release of API during the later part of the release profile when the diffusional release is beginning to slow down because of possible decrease in the API concentration or an increase in diffusion pathlength. This may help to keep the release profile closer to zero-order than would otherwise be the case. It is possible that such increased diffusivity could provide a boost to the release rate during the later part of the release when the API concentration, which drives the diffusion, has already decreased, thereby countering the natural tendency of the release to tail off.

After being administered to a patient, the units may pass entirely through the patient's digestive system while retaining approximately their original dimensions, since a diffusion-controlled dosage form may typically be designed so that only the API leaves the dosage form.

It is possible, as mentioned, that a dosage form may comprise multiple units that are not identical to each other. For example, various units may have the same API but different release profiles as a result of, for example, different wall thicknesses, or could be quick release as a result of having no wall, or some units could have delay times. In this event, the overall release profile from the entire dosage form may be calculated as a sum or superposition of the release profiles of individual units. For example, the overall release profile could be something other than zero-order. The overall release profile could, for example, be chosen so as to give a desired time history of blood concentration of API.

The present invention is further described but is in no way limited by the following non-limiting Examples. These Examples describe various steps of materials evaluation, construction of dosage forms, in vitro testing of dosage forms, and in vivo testing of dosage forms.

EXAMPLE 1

Drop Testing

For rapid screening of candidate materials, a drop test was used to gain understanding of interactions between potential binder liquids and potential powders. This test included dropping a drop of a potential binder liquid onto a bed of a potential powder and visually observing the interaction. In such a test, the main observation was a qualitative observation of the infiltration of binder into powder, such as the rate of infiltration. The dropping of drops was done by hand, and the drop that was dropped was substantially larger than a dispensed drop from an actual printhead in three-dimensional printing, but still the observations were qualitatively useful. For construction of a core-shell structure, both core and shell binders need to be absorbed into the powder before the next pass of powder spreading. Slow infiltration results in insufficient time for the interaction to take place. There is also some disadvantage for excessively rapid infiltration in that it can cause undesirable bleeding into the local regions not intended to receive liquid.

The drop tests were performed on various different grades of Ethyl celluloses (EC), Eudragit RSPO and Kollidon SR. It was learned from the drop tests that the interaction of the aqueous pseudoephedrine hydrochloride (PEH) solution (the API-containing liquid) with the release blocking polymers other than Kollidon SR was too slow for the liquid to be absorbed into the powder bed during printing. This may be related to the fact that such polymers have some degree of hydrophobicity, which hinders the interaction with the aqueous binder. For ECs and Eudragit RSPO in particular, no infiltration of aqueous PEH liquid into the powder was observed even over a period of several hours. From the drop test for ECs and HPMCs, the distinction in infiltration time between different grade polymers within the same category was not clear. The influence of particle size was more significant than was the influence of the molecular weight of the polymer. Large particles resulted in shorter infiltration time than small particles. It was also observed that infiltration was significantly improved by addition of 30% and 50% of microcrystalline cellulose (Avicel PH 301) or spray dried dicalcium phosphate (Fujicalin S) to the powder bed. On the other hand, the third category out of those three categories of substances, Kollidon SR, exhibited relatively short (good) infiltration time (of the order minutes) in the drop tests. Accordingly, Kollidon was chosen as the material for the release-blocking polymer in the two-polymer powder mixture.

Drop tests were also performed with ethanolic liquids resembling the eventual shell binder liquid. It was observed that the infiltration of ethanolic binders with high ethanol contents into the polymers being tested was much more rapid than the infiltration of the PEH-containing liquid, and was certainly an adequate infiltration rate for use in three-dimensional printing. Absorption of these ethanolic fluids could even be so rapid as to result in excessive bleeding of the liquid through the powder, although parameters such as saturation parameter can further be varied somewhat to control bleeding. In regard to the shell binder liquid, the drop tests led to selecting a shell binder liquid that was a solvent, for at least some polymer particles.

EXAMPLE 2

Printing of Primitive Shapes Such as Lines and Ribbons

After some screening of materials by drop testing, further materials and process characterization was also performed by printing primitive shapes such as simple lines and ribbons on a powder bed using various combinations of materials, flowrates and drop-to-drop spacing and line-to-line spacing. In addition to illustrating interactions between the powder and the liquid beyond what was observed in the drop tests, the tests involving the printing of primitive shapes also served to identify the binder solutions which cause least geometric deformation (swelling or warping), and to identify the most appropriate drop-to-drop spacing and line-to-line spacing and layer thickness for specific liquids so as to give appropriate structural integrity. The powder upon which these line and ribbon tests were performed was either Eudragit RSPO or Kollidon SR. Even if the powder was not the exact powder ultimately used for fabricating dosage forms, the general findings obtained are still considered applicable to the powder that was eventually used for making the dosage forms. A nozzle with an orifice of <0.0075 inch (190 micrometers) was used. Three different liquids were used.

Various drop-to-drop spacings were used to print individual lines on Eudragit RSPO powder. This demonstrated that the line diameter was decreased when 15% TEC was added to the ethanol-water (75:25) solution, and was further decreased by addition of 6% RS PO to ethanol-water-TEC binder. Each of these changes resulted in an increase in the viscosity of the dispensed liquid, and so these results basically illustrated that more viscous binder resulted in less bleeding and hence decreased line diameter. When single lines were printed, using a drop-to-drop spacing of 600 micrometers, the final dimension of the lines was approximately 0.4 mm and 0.5 mm for flow rates of 0.75 g/min and 1.0 g/min respectively. Based on these results, in order to keep the shell thickness to a reasonably small value (consistent with unit dimensions which are comfortable for swallowing, and given the desire to preserve a substantial volume for deposition of API), the shell it was decided that in most units or dosage forms the shell would be printed such that the thickness of the shell is only two drop-to-drop spacings or line-to-line spacings or layer thicknesses. In this case, as in all other descriptions herein in which a flowrate is reported, the liquid was dispensed at intervals in time of $\frac{1}{800}$ second.

A ribbon is a collection of lines adjacent to each other and binding with each other. The purpose of a ribbon test was to optimize the line-to-line spacing. Drop-to-drop spacings (DDS) in the range of 300 to 600 micrometers were also evaluated. Dimensions and weights of ribbons were measured after drying. Samples were visually inspected and judged for strength and integrity on a qualitative basis.

The same liquids used for line tests were also used for the ribbon test, which was similarly performed by printing onto Eudragit RSPO powder. The results from ribbon test were as follows:

- Ribbons became thicker with tighter line-to-line spacing because binder liquid seeped down below the printed area. The number of defects (cracks and holes) increased with increasing line-to-line spacing.
- The weakest ribbons were obtained when printing with aqueous PEH-containing liquid, due to the limited binding among the polymer particles that occurred with this liquid. This liquid also resulted in the least swelling and deformation at low line-to-line spacings, which was probably also due to the minimal interactions with polymer particles. However, this liquid was only intended for use in the core, where binding of particles to each other would not be important anyway.

Shell binder liquid with 15% TEC and 6% Eudragit RSPO created strong ribbons with significantly more cracks and lumps than the shell binder liquid without Eudragit RSPO. The defects could result from insufficient dissolution of polymer particles due to increased viscosity of the shell binder liquid that did contain Eudragit RSPO.

Results for various combinations of line-to-line spacings and drop-to-drop spacings are shown in the parameter map given in FIG. 6. For the data reported in FIG. 6, the shell binder liquid dispensed onto the powder was an ethanol-water solvent containing dissolved TEC without a viscosity enhancer. The powder printed upon was Kollidon SR. The qualitative criteria for judging the quality of ribbons included the number of defects, the strength of the ribbon, and the ease of harvesting the printed ribbon from the powder bed. The range for appropriate combinations for line-line spacings and drop-drop spacings was similar for three different liquids tested. As a result of this testing, it was decided to use a drop-to-drop spacing of 400 micrometers and also a line-to-line spacing of 400 micrometers. The layer thickness was also chosen to be 400 micrometers.

EXAMPLE 3

Testing of Diffusion or Leakage Through a Film

Figure 7:
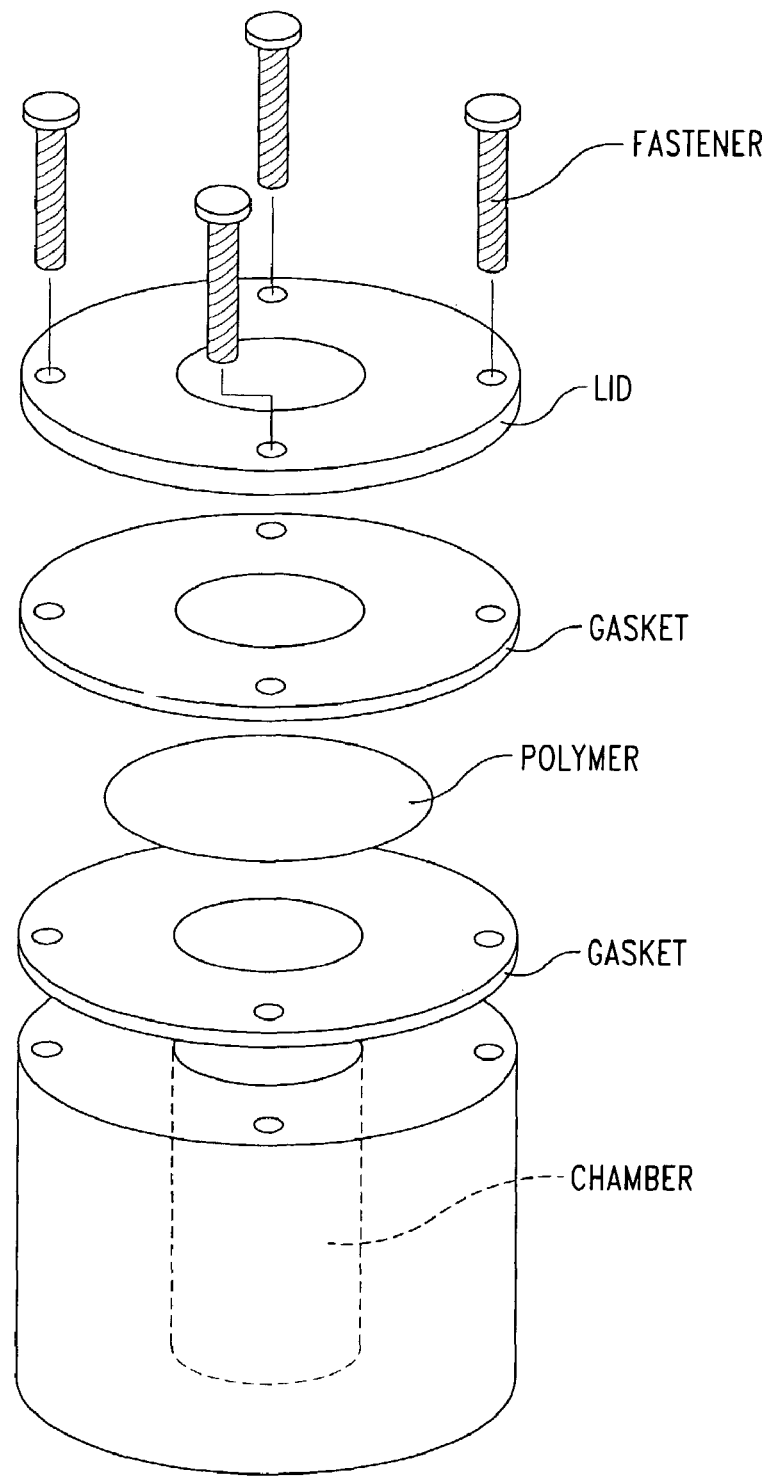
FIG. 7 illustrates an apparatus used for testing diffusion through films made by 3DP according to principles of the present invention.

This experimentation was done in order to characterize the diffusion behavior of a film or membrane of a candidate composition, and especially to characterize the presence or absence of pinholes and similar defects that would affect diffusion of API from a dosage form. Visual observation might provide some assessment of the presence or absence of pinholes that can be seen, but a test for pinholes that is more direct and pertains more closely to the final application would involve exposing a film to liquid and measuring the passage of substances through the film. Accordingly, for this test, flat films were printed by 3DP just like the previously described ribbons, using selected materials, a designated flowrate of shell binder liquid and either one or two powder layers. The material used as the powder was a single material, i.e., only the release-blocking polymer, not the combination of two different types of polymers which is described elsewhere herein for making actual dosage forms. After printing and harvesting, the film was tested by being clamped all around its perimeter in a leak-tight manner and exposed on one side of the film to an API-containing liquid and on the other side of the film to simulated gastric fluid. The apparatus is shown in FIG. 7. The apparatus that clamped the test material and exposed it to an API-containing liquid was submerged in the liquid (dissolution medium) in a dissolution cell, in a position such that the film was at the bottom of the apparatus, to insure that any air bubbles contained inside the apparatus would float away from the film. In this experimental arrangement, the only path for release of API from the apparatus to the outside liquid (dissolution medium) was diffusion or leakage through the film itself. It can be noted that the liquid on the source side of the film was a simple liquid solution, without any solid solute being present along with the liquid, i.e., the liquid solution was not saturated.

From this experimentation, it was determined that a single-powder-layer film printed with a relatively small flowrate consistently leaked, but films which were either two-powder-layer or single-powder-layer printed with a larger flowrate maintained their integrity. For construction of actual dosage forms, it was decided to construct the shell using a film of two layers thickness in order to provide good confidence concerning the absence of defects.

In regard to the use of Kollidon SR as the powder, in the shell region the major polymeric component of Kollidon SR, namely PVAc, becomes fused by the ethanolic shell binder liquid due to the high solubility of PVAc in ethanol. The subsequent drying process at 50° C. for 12 hours effectively cured PVAc, which has a low glass transition temperature (35° C.) even in its unplasticized state, to form an impermeable barrier to completely block the release other than through the hydrated HPMC if HPMC is included in the powder. As for the Kollidon SR, it might be wondered if the presence in Kollidon SR of a minor component that is water-soluble, namely PVP K30 (polyvinyl pyrrolidone, molecular weight 30,000 Daltons) that is present in the amount of 19%, might have any diffusive or release-regulating behavior. Accordingly, as a related experiment, some units were manufactured using only Kollidon SR powder, containing no fraction of release-regulating polymer such as HPMC. In these dosage forms, no release at all from the dosage form was observed within 24 hours. This suggests that the PVP K30 does not have any part in facilitating the release of API in the dosage form of the present invention. It was concluded that in dosage forms of the present invention involving Kollidon and HPMC, API is released only through the HPMC paths or network.

EXAMPLE 4

Testing Procedures Pertaining to In Vitro Dissolution Testing

Tests were performed by manufacturing dosage forms or units and then dissolving them in a liquid dissolution medium to obtain in vitro dissolution data which simulated in vivo conditions as closely as possible. Because it is not possible to predict exact conditions in the digestive tract of an actual patient, the formulations were tested under a variety of dissolution conditions, including varying the pH of the dissolution medium, the paddle stirring rate in the dissolution cell and the presence/absence of a sinker which (if used) served to keep the dosage forms submerged during dissolution testing. The number of units tested at any one time was varied together with the size of the dissolution chamber.

Dissolution tests were performed in an 8-station dissolution test apparatus (VK 7000, VanKel Industries, Inc., Cary, N.C.) using a USP Apparatus II method and water or aqueous solutions as the dissolution medium. Dissolution media used included 0.1 N HCl solution having a pH of 1.2, and phosphate buffer solutions having pHs of 6.0 and 7.4, in order to evaluate the pH sensitivity of the dosage forms. The temperature of the dissolution medium was controlled at 37±0.5° C. The paddle speed was 50 rotations per minute, except when it was varied to 150 rpm to test the influence of that variable. Single units were used for dissolution studies except that some tests were performed for the purpose of in vivo-in vitro correlation, using 8 units encapsulated four units each in each of two #00 gelatin capsules (Gelcaps). Dissolution vessels of 200 mL and 900 mL were used for studies with single units and 8 units, respectively. In most tests, the dosage forms were placed in a stainless steel cage in the dissolution vessels to prevent floating, while in other tests the dosage forms were allowed to float.

There was not a large difference in dissolution rates for any of these variables. In regard to the insensitivity of dissolution to pH within the pH range of 1.2 to 7.4, the pH insensitivity resulted from the pH insensitivity of the active and the materials used for the formulations. The insensitivities of these formulations to various dissolution conditions suggests that the release profile of the dosage forms of the present invention should not be sensitive to the presence/absence of food in the stomach of a patient.

It is believed that the insensitivity of the release profile to paddle rotational speed supports the explanation that API release from the manufactured dosage forms was dominated by diffusion. There was essentially no change in release profile when the paddle speed was increased from 50 rotations per minute to 150 rpm, for the nominal 8-hour formulation. It is believed that the insensitivity of the release profile to paddle rotational speed suggests that for present conditions there is minimal or no erosion of HPMC during the release of API.

EXAMPLE 5

Manufacturing of Dosage Forms

Manufacturing of the Example dosage forms was performed on a 3DP machine. The powder used was a mixture, in specified ratios, of Kollidon SR (BASF Corp., Shreveport, La.) and hydroxypropylmethyl cellulose, substitution type 2910 (Pharmacoat 603, Shin-Etsu Chemical). Kollidon SR is a mixture of 80% polyvinyl acetate (PVAc) with a molecular weight of 450,000 Daltons, 19% polyvinylpyrrolidone with a molecular weight of 30,000 Daltons, and small amounts of sodium lauryl sulfate as a surfactant and silica as a stabilizer. The Kollidon was the release-blocking polymer and the hydroxypropylmethyl cellulose was the release-regulating polymer. These two materials were mixed using a twin shell blender for 15 minutes before fabrication. Three different ratios (by weight) were used, namely Kollidon SR-HPMC ratios of 80:20, 70:30 and 60:40. The 80:20 ratio was formulated to give the slowest release, and the 60:40 ratio the fastest release. Some data were also taken with a 40:60 ratio.

Three-dimensional printing was performed using primitive dimensions that were a layer thickness of 400 micrometers, a drop-to-drop spacing of 400 micrometers, and a line-to-line spacing of 400 micrometers. Drops were dispensed at intervals of $1/800$-second, and the printhead was moving at a rate of 400 microns for each $1/800$-second, or 0.32 m/s.

The flowrate of shell binder liquid which reliably gave defect-free shells was at least 1.8 g/min when the binder liquid was being dispensed at every consecutive droplet dispensing interval or every possible drop location at a droplet dispensing frequency of 800 Hz. The density of the shell binder liquid was 1.07 g/milliliter, so this means that the volume of an individual drop was 3.5E−11 m^3. The overall volume of a voxel was 6.40E−11 m^3. The ratio of these two quantities is 0.55 milliliters of shell binder liquid per milliliter of overall voxel volume. The packing density of the powder was not exactly known, but if the packing density were a typical value of 50%, then the saturation parameter would be slightly more than 1 (i.e., approximately 1.1).

The shell binder liquid was approximately 15 wt % triethyl citrate (Spectrum Chemicals), together with approximately 85 wt % of an ethanol-water mixture, the ethanol-water mixture comprising approximately 75 wt % ethanol and 25 wt % water. The triethyl citrate was present as a plasticizer.

The shell region was fabricated with a shell binder flow rate of 1.8 g/min. The shell binder liquid was dispensed through a microvalve and thence through a nozzle having an inside diameter of 0.003 inch (76 micrometers) or 0.004 inch (102 micrometers). Although other shell binder liquid flow rates were tested, 1.8 g/min was found to provide sufficient saturation to form a continuous shell free from pinholes.

The API-containing liquid dispensed into the core was approximately 50 wt % pseudoephedrine hydrochloride, approximately 5 wt % polyvinyl pyrrolidone (molecular weight 17,000 Daltons, BASF Corp.), approximately 0.1 wt % of a surfactant which was Tween 20 (Spectrum Chemicals), with the balance of the composition being water. The API-containing liquid was dispensed through a microvalve and thence through a nozzle having an inside diameter of 0.0075 inch (190 micrometers). The flow rate of API-containing liquid was controlled at 2.1 g/min when a drop was being dispensed at every voxel under the specified conditions. The unit, dimensioned as above and printed in the core with this liquid, was able to contain 7.5 mg of pseudoephedrine hydrocholoride, meaning that an assembly of eight units could contain 60 mg. This API is a relatively high-dose API. The units as printed were approximately cubical with an overall external side length of 4.6 mm. They had a core-shell structure with a shell thickness of 0.8 mm. The core had a side length of 2.8 mm. The placement of 7.5 mg of API in a core volume of 2.8 mm on each side of a cube, resulted in an API volumetric content of 0.34 mg API per mm^3 of core region.

The fabricated dosage forms were oven dried at 50° C. for 12 hours and were hand dedusted using a sieve to remove the excess unbound powder particles.

EXAMPLE 6

Physical Stability of Dosage Forms

A stability test was performed on the 12-hr formulation to determine the influence of high temperature and humidity on the dissolution properties. The dosage forms were stored at 25° C., 60% Relative Humidity and at 40° C., 75% Relative Humidity, in open and closed containers. Dissolution studies were performed on the samples at 1, 2 and 4 weeks. No significant changes in release characteristics were observed after a 4-week storage period for each of the samples in an open container condition. The excellent physical stability of the formulation may result from the drying conditions to which the dosage forms were exposed during manufacture. The dying step, which was part of the manufacturing process, which was 12-hour exposure to 50° C., effectively cured the major polymeric component of the Kollidon SR, namely polyvinyl acetate, which has a low glass transition temperature (42-45° C.) even when it is in an unplasticized state. The residual amount of ethanol in the nominal 12-hour formulation (after the drying step) was also evaluated using a Gas Chromatograph method and was found to be less than 1.2%.

EXAMPLE 7

Figure 8:
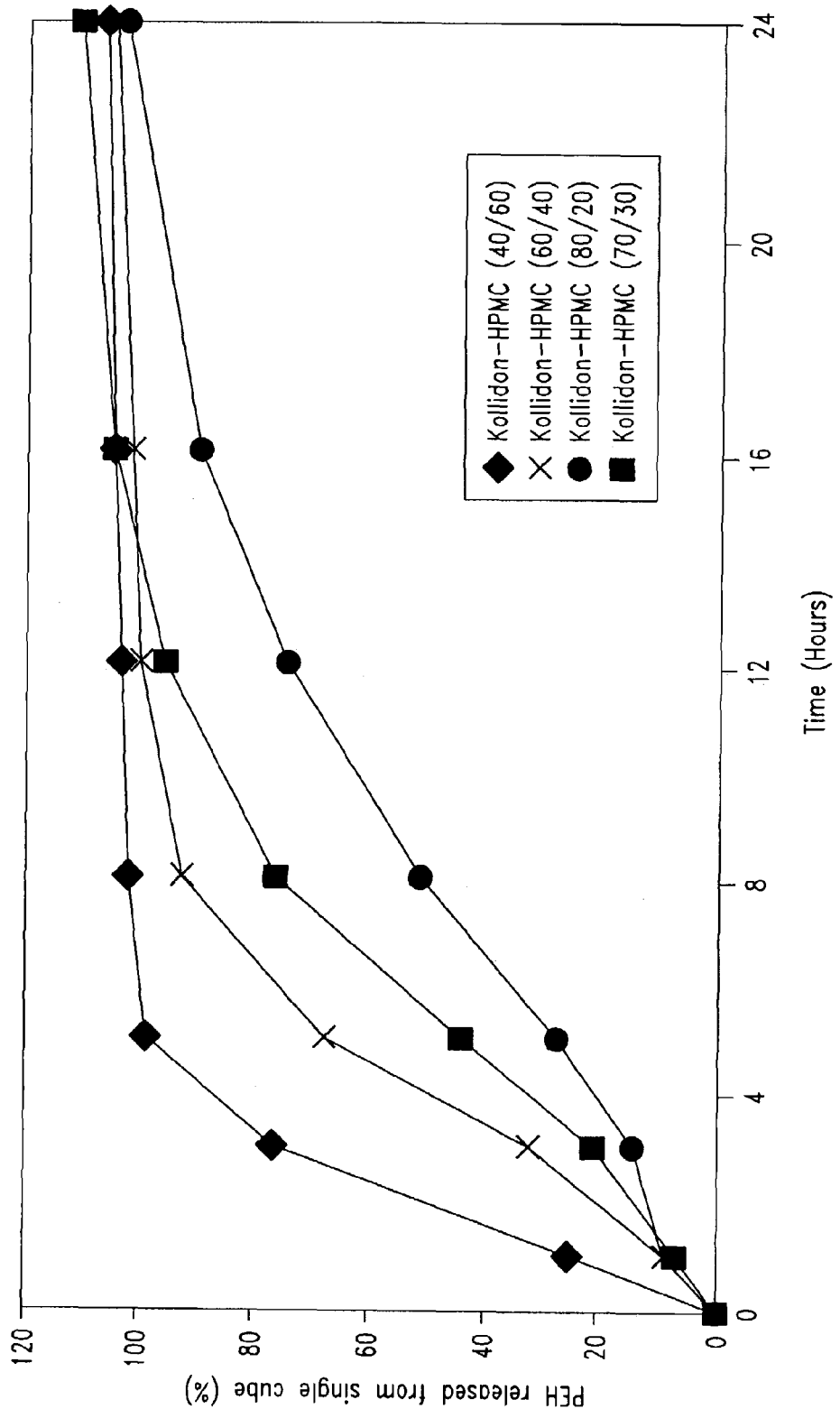
FIG. 8 is a chart illustrating release of API over time from dosage forms of the present invention having four different time scales of release according to principles of the present invention.

In Vitro Dissolution Including Adjustment of Overall Time Scale of Release Profile by Adjustment of Proportions of Two Polymers Units were manufactured as described elsewhere herein and were tested using the in vitro dissolution testing procedures described elsewhere herein. Three different ratios of powder components were used. The Kollidon:HPMC ratio of 60:40 was intended to provide a release profile that released in approximately zero order fashion over a nominal 8 hour time period. The ratio of 70:30 was intended to provide a nominal 12-hour release profile. The ratio of 80:20 was intended to provide a nominal 16-hour release profile. An even faster release profile of approximately 4 hours was achieved with a Kollidon:HPMC ratio of 40:60. FIG. 8 shows that these desired time frames were achieved. Although it is not shown in the Figure, repeatability among dosage forms manufactured at different times was good.

The in vitro release profiles of the various formulations are demonstrated in FIG. 8. The overall in vitro release rates of the three formulations were close to their corresponding target release rates. The F2 statistics, used to compare the observed release profiles to the target profiles, were higher than 50% for all of the three formulations, demonstrating the similarity between the observed and target zero-order release profiles. Furthermore, every data point in the dissolution profiles of the three formulations deviated from the corresponding target release by less than 10%, except for the 16-hour data point for the nominal 16-hour formulation. Except for the nominal 16-hour formulation, the other two formulations were able to release drug to nearly 100% within the target time. For nominal 16-hr formulation, it is known that the drug was released following zero-order kinetics up to approximately 75% at the $12^{th}$ hour. The release rate between 12 and 16 hr is not known because no sample was taken during this period of time.

As a separate experiment leading up to the data just described, some dosage forms were manufactured containing only an API-containing core that was essentially identical to the core in the described units or dosage forms, with no shell around the core. The purpose of this experiment was to confirm that the core itself was a rapid release, in order to confirm that whatever control of the release profile was obtained really was due entirely or almost entirely to the properties and behavior of the shell. As expected, the core-only dosage forms released their API very quickly. Thus, the shell is the dominant factor determining the release profile.

It can also be noted that the dosage forms whose release profiles are shown in FIG. 8 did not exhibit an initial burst release, which is a sometimes undesirable feature that often occurs with other designs of dosage forms. It is believed, although it is not wished to be restricted to this explanation, that the fact that the shell may be free of API, together with the fact that it takes a certain amount of time for the HPMC in the shell to hydrate and form paths which can support diffusion, helps to avoid the initial burst release feature which often occurs with other designs of dosage form. The dosage forms whose release profiles are shown in FIG. 8 did not contain a buffer region (results for dosage forms which include a buffer region are given in the next example), and even without a buffer region they still did not exhibit any initial burst release. The shell for the dosage forms in this study was approximately 0.8 mm thick, much thicker than that typically obtained from the traditional film coating process. As a result, it took some time for HPMC in the shell to complete the hydration process to transition from the glassy state to the rubbery state so that the API could diffuse out of the dosage forms. It is believed, although not wishing to be restricted to this explanation, that this time-dependent hydration process in the shell was helpful in eliminating the initial bursting release, commonly observed with traditional reservoir type controlled release dosage forms.

EXAMPLE 8

Figure 9A:
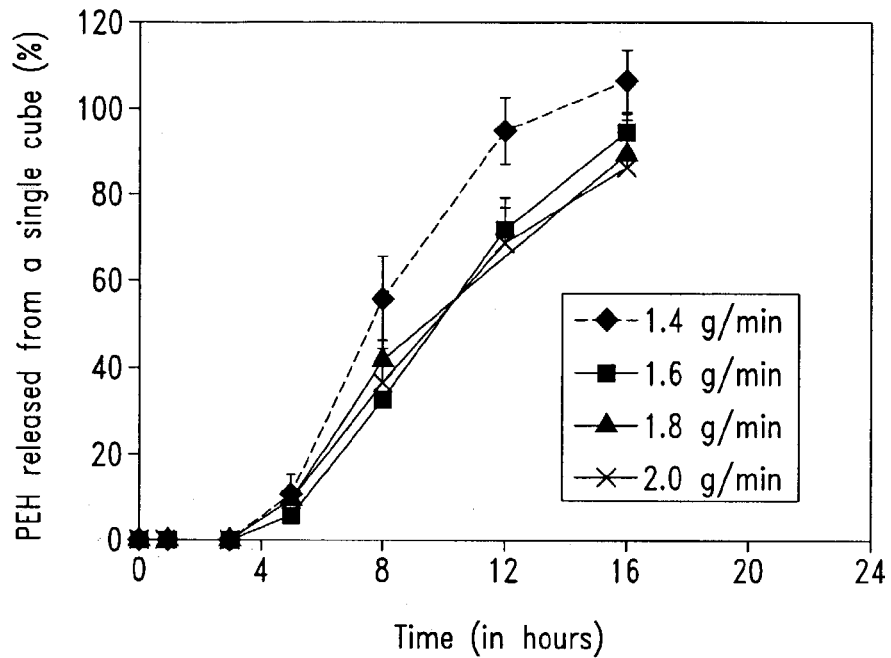
FIGS. 9A and 9B are charts illustrating release of API from dosage forms of the present invention comparing the presence or absence of a buffer region, illustrating the existence of a delay time when the dosage form contains a buffer region according to principles of the present invention.
Figure 9B:
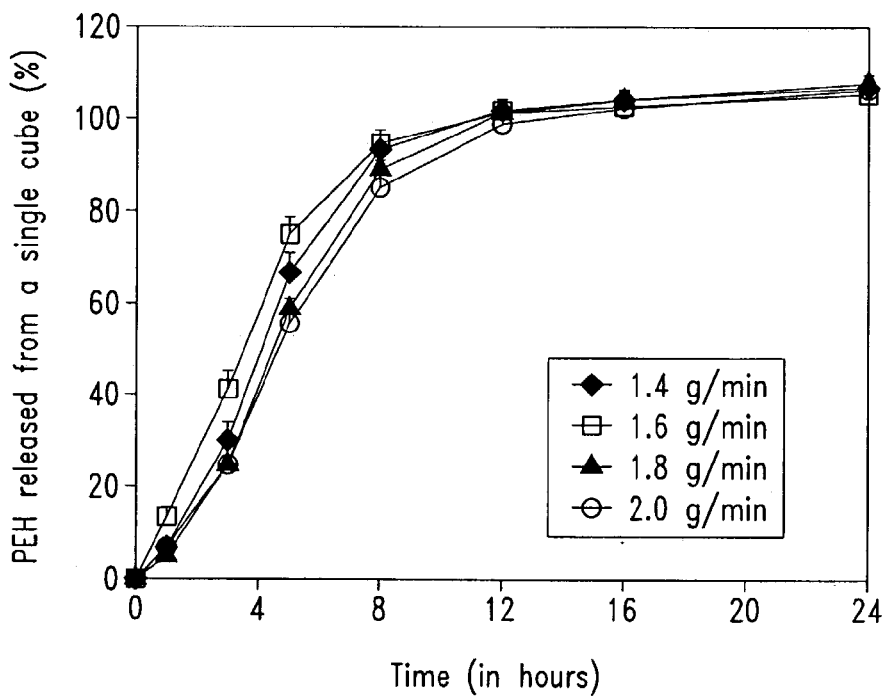

In Vitro Dissolution Illustrating a Delay in Start of Release When a Buffer Region Exists Units were manufactured, as described elsewhere herein, both with and without a buffer region. When a buffer region was included in the dosage form, it had a thickness in all directions of two voxel units (two drop-to-drop spacings, two line-to-line spacings, two powder layer thicknesses) or approximately 800 micrometers, the same as the shell itself. The release profiles of units both with and without a buffer region were measured in the dissolution apparatus, and are shown in FIG. 9. It can be seen that the use of a buffer region of 800 micrometers thickness resulted in a delay of several hours in the start of release, compared to the release from a unit that had no buffer region. Part of the reason why the buffer region causes a delay may be time needed for the buffer region to hydrate. This data was taken with the formulation having a Kollidon SR:HPMC ratio of 60:40. The drug release from this dosage form was completely blocked for at least 3 hours.

EXAMPLE 9

In Vivo Study

The dosage forms made as described previously, containing pseudoephedrine hydrochloride were administered to human subjects. The concentration of API in the subjects' blood was measured at designated times following administration of the dosage forms.

The in vivo study was a single-dose, randomized, open-label, four-way crossover study. Ten normal adult male subjects between the ages of 21 and 28 and within ±15% of their ideal body weight according to the 1983 Metropolitan Height and Weight table were enrolled in this study after medical screening. The subjects were admitted to the clinic site for each phase at least 12 hours prior to dosing and were released after the 36-hour post-dose blood samples were taken.

For subjects that received the dosage form of the present invention, four units of the formulation were manually inserted into a #00 gelatin capsule, and two capsules were administered to each subject. As a reference formulation, subjects were also administered Sudafed Immediate Release Tablets (GlaxoWellcome, South Africa) containing 60 mg of the same Active Pharmaceutical Ingredient. The dosage forms that were used as a control released all of their API within a short period of time after being administered to a patient.

The dosing schedule of the four formulations was determined using a random number table. Each subject was randomly assigned to one of the four sequences to receive a single dose of 60 mg PEH after fasting for 10 hours. The subjects continued to fast until 4 hours after dosing, then a standard lunch was served. During each phase of the study, 7 ml venous blood sample were collected from each of the subjects immediately prior to drug administration (0 h) and at 0.25, 0.5, 1.0, 1.5, 2.0, 3.0, 4.0, 6.0, 8.0, 10, 12, 16, 20, 24, 30 and 36 hours after administration. The samples were transferred immediately into pre-cooled Li-Heparin containing test tubes. After centrifugation at 2000 rpm for 15 minutes, plasma samples were harvested and stored at −80° C. until analysis. The pseudoephedrine plasma concentrations were analyzed using a validated LC/MS/MS method with an LOQ of 1.55 ng/mL.

TABLE 1

Pharmacokinetic Parameters of Three Test Formulations and Reference Formulation Mean (% RSD)

| Formulation | $C_{max}$* (ng/mL) | $T_{max}$* (hr) | $AUC_{(\infty)}$ (ng·hr/mL) | | $K_{el}$ (hr$^{-1}$) | $T_{1/2}$ (hr) | $F_{rel}$** (%) |
|---|---|---|---|---|---|---|---|
| 8-Hour | 149 | 7.0 | 1942 | 1972 | 0.1425 | 5.0 | 99 |
| | (18.9) | (15.1) | (22.2) | (22.2) | (16.4) | (21.2) | |
| 12-Hour | 123 | 9.2 | 1775 | 1808 | 0.1390 | 5.0 | 93 |
| | (17.4) | (18.3) | (17.5) | (17.5) | (10.5) | (10.9) | |
| 16-Hour | 98 | 9.6 | 1665 | 1712 | 0.1309 | 5.3 | 89 |
| | (25.5) | (21.5) | (22.3) | (21.7) | (10.7) | (10.9) | |
| Sudafed | 198 | 1.6 | 1831 | 1849 | 0.1469 | 4.9 | 100 |
| | (17.3) | (37.9) | (18.5) | (18.5) | (18.9) | (17.0) | |

Figure 10:
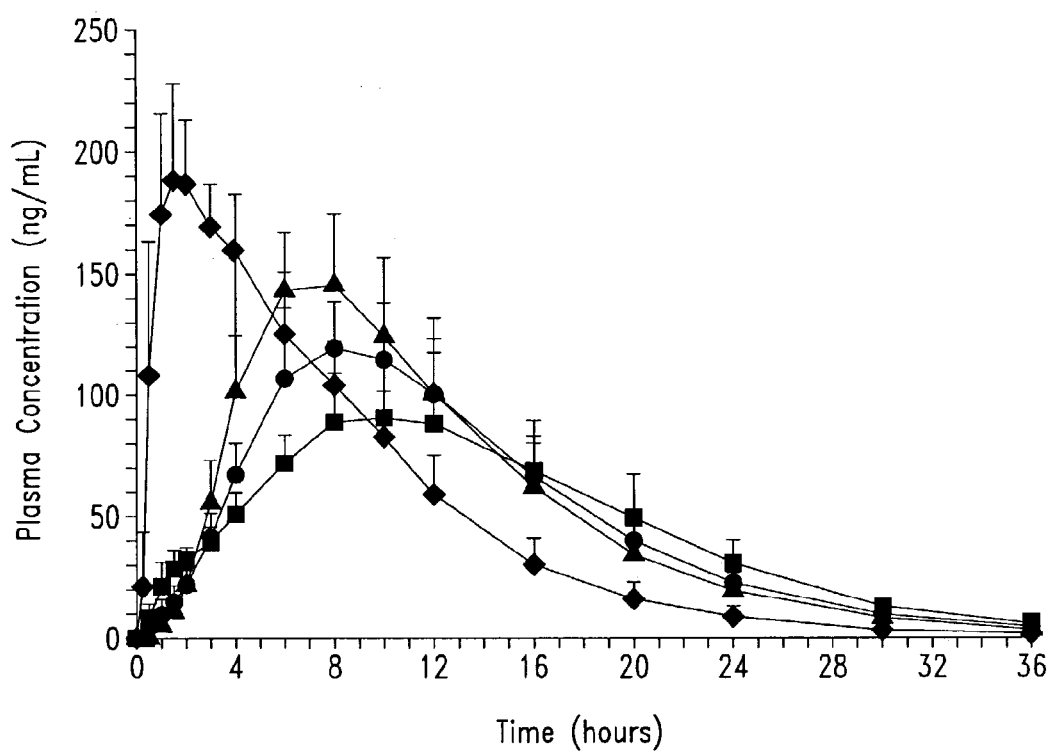
FIG. 10 is a chart illustrating results obtained from in vivo testing, in the form of concentration of API over time in the blood plasma of humans to whom the dosage forms were administered according to principles of the present invention.
Figure 11A:
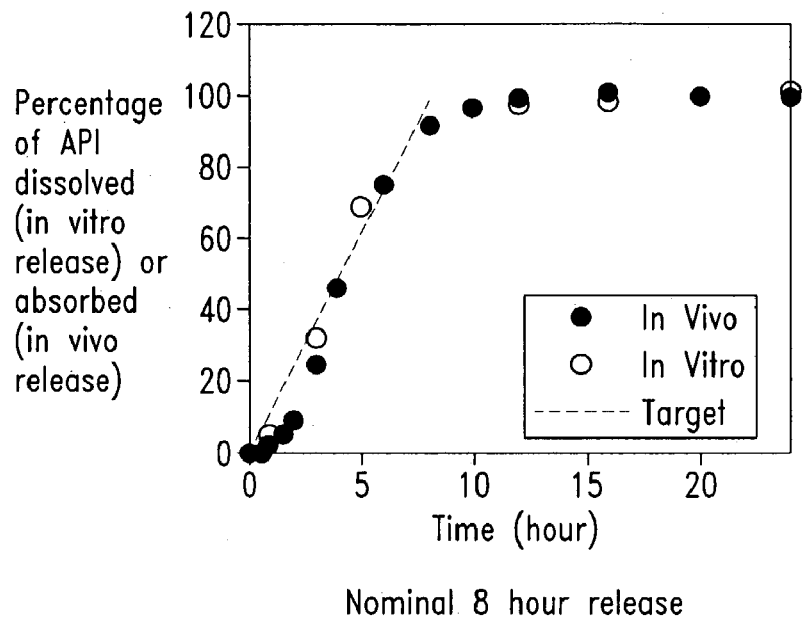
FIGS. 11A-11D illustrates comparisons between in vivo release and in vitro release according to principles of the present invention.
Figure 11B:
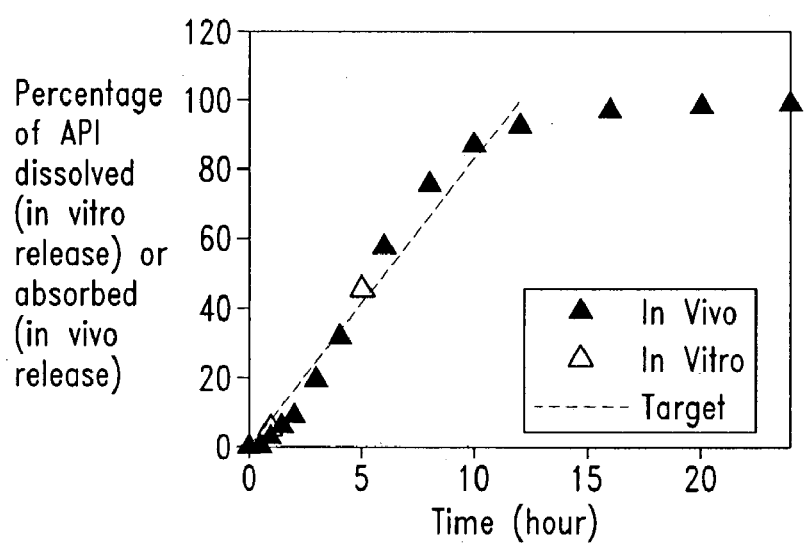
Figure 11C:
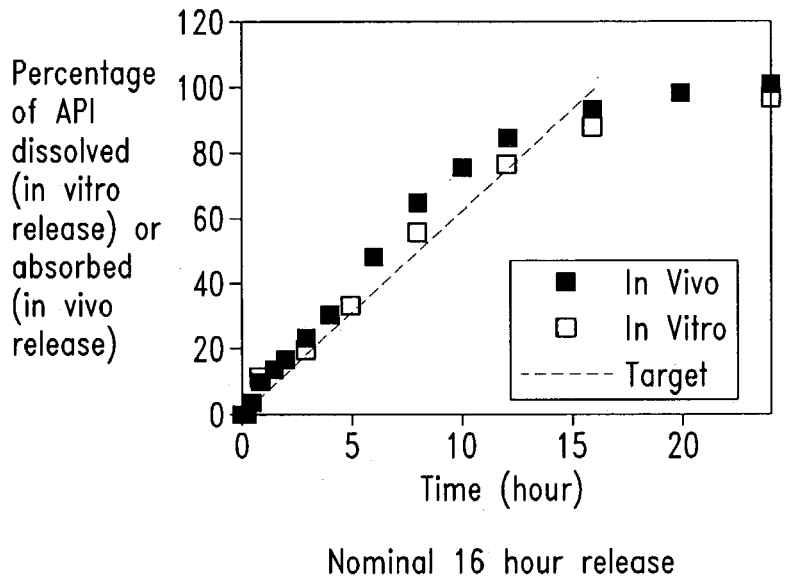
Figure 11D:
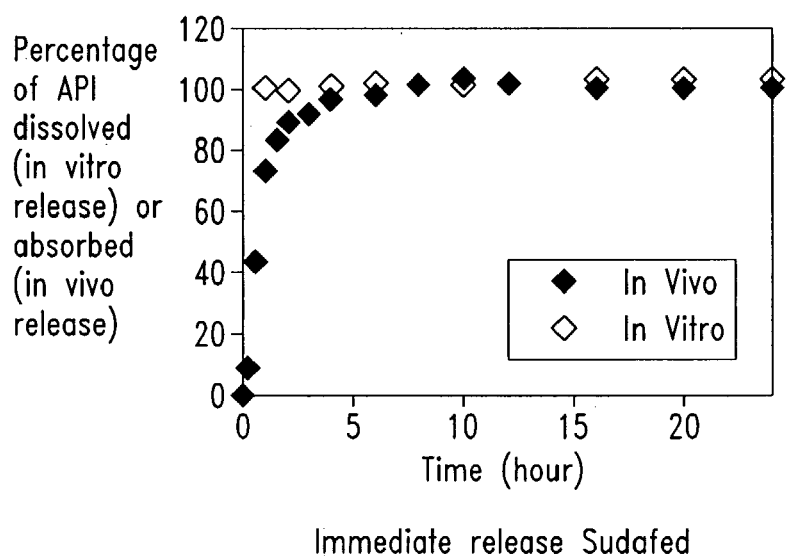

*$C_{max}$ for all formulations were significantly different from each other; $T_{max}$ for all formulations were significantly different from each other except for 12-hour and 16-hour formulations, the data were analyzed at 95% CI using 2 Tailed T-test.
Relative bioavailability, obtained from the ratio of $AUC_{(\infty)}$ of the test formulation to $AUC_{(\infty)}$ of the reference formulation The plasma concentration-time curves for the three test formulations and the reference formulation are displayed in FIG. 10**. In accordance with the in vitro dissolution profiles, the plasma profiles demonstrated a clear distinction between the formulations. The low variation of the plasma level data within the same formulation suggested the reproducible in vivo performance of the dosage forms. The pharmacokinetic parameters, calculated from the plasma concentration-time curves, are shown in Table 1. The $C_{max}$ values of the tested formulations decreased when the duration for drug release extended, as expected. The $C_{max}$ values of different formulations were also significantly different from each other. The $T_{max}$ values for the 12-hr and 16-hr formulations were not significantly distinguishable, however, both were significantly longer than the 8-hr formulation and the immediate release reference product. The relative bioavailability decreased slightly when the release duration was prolonged from the nominal 8-hour release to the nominal 12 hour release and to the nominal 16 hour release.

The plasma pseudoephedrine concentrations above the LOQ were used for pharmacokinetic analysis. Pharmacokinetic parameters were calculated using the SAS System Statistics program (SAS Institute Inc., Cary, N.C., USA) with the TPD (Therapeutic Products Directorate of Canada) macro PKVARM SAS. Ninety percent confidence intervals for ANOVA comparison of $C_{max}$, the area under the plasma concentration-time curve from time 0 to t, $AUC_{(0-t)}$, and from time 0 to infinity, $AUC_{(0-\infty)}$, were calculated between all formulations using SAS with the TPD (Therapeutic Products Directorate of Canada) macro ANOVSM.SAS. The $AUC_{(0-t)}$ was calculated using trapezoid method. $AUC_{(0-\infty)}$ was obtained by extrapolating $AUC_{(0-t)}$ to time infinity by the following equation:

$$AUC_{(0-\infty)} = AUC_{(0-t)} + \frac{C_{(t)}}{K_e}$$

Where $C_{(t)}$ is the plasma concentration of pseudoephedrine HCl at time t, and $K_e$ is the elimination rate constant, calculated as the negative value of the slope by linear regression of the terminal phase of the semilog plasma drug concentration-time profiles. The relative bioavailabilities ($F_{rel}$) of the test formulations were the ratios of their $AUC_{(0-\infty)}$ values to the $AUC_{(0-28)}$ of the reference formulation. The $F_{rel}$ values were derived for each subject and the arithmetic mean of ten subjects was used to represent the $F_{rel}$ of each test formulation.

The absorption profiles for each individual subject were deconvoluted using Wagner-Nelson method (Wagner & Nelson, 1964):

$$\% \text{ Absorbed} = \frac{C(t) + K_e AUC_{(0-t)}}{K_e AUC_{(0-\infty)}} \times 100$$

The in vivo-in vitro correlations were established using the mean dose absorbed and the mean cumulative drug dissolved data. Linear regression was used to examine the extent of the correlation. After regression analysis, the difference between intercept values and zero was determined and the difference between the slope and unity were determined using t tests.

The cumulative in vitro release profiles of three formulations demonstrated good agreement with their corresponding in vivo absorption profiles, obtained using Wagner-Nelson method, as shown in FIG. 11. The in vitro release and the in vivo absorption plots were nearly superimposable for the three test formulations, indicating that the absorption of the active mainly depended on the release rates of the dosage forms. The linear regression analysis of the in vivo and in vitro data also suggested a significant linear in vivo-in vitro correlation. The slopes of the three test formulations are all close to unity, suggesting that the in vivo and in vitro release rates were similar. Alternatively, the release of active from the reference formulation was so rapid as to exceed the absorption rate, as indicated by the lower slope value. Furthermore, the intercepts of the three test formulations were all close to the origin, indicating the immediate absorption of active following administration.

Further Considerations and Summary and Advantages

Diffusion-controlled dosage forms have been successfully developed using a core-and-shell geometry that can be made by three-dimensional printing. The dosage forms may have approximately a zero-order release profile. The time scale of the release profile can easily be altered by adjusting the ratio of the two types of polymers powder used in making the overall powder. Formulations having nominal release durations of 8, 12 and 16 hours, and also 4 hours, have been demonstrated. The release rates of the formulations increased with the fraction of HPMC in the polymer powder blend, due to the increased diffusion pathways for drug release. Defect-free shells have been fabricated even while other parts of the dosage form are porous. The manufacturing methods described have produced dosage forms which were consistent and repeatable and gave expected release profiles in both in vitro and in vivo tests. The manufacturing methods described produce the entire dosage form essentially in one process using only one powder raw material, rather than producing one part of the dosage form in one operation and another part in another operation.

If desired, it would also be possible to perform three-dimensional printing onto a powder bed that contains particles of a release-blocking polymer and particles of a water-soluble substance. For example, lactose or mannitol could be used. This would make a micro-porous membrane (resembling that which is described in Kim, Controlled Release Dosage Form Design), but by a different method which would be a single-process manufacturing technique. Also, such a membrane could be substantially thicker than the membrane of Kim, which was made by a coating technique.

Another possibility is applying the combination of release-blocking polymer and release-regulating polymer, in the form of a shell, by a method other than the disclosed three-dimensional printing. Although such alternatives would involve more individual manufacturing steps, they are certainly possible. For example, the combination of the two powders perhaps together with a carrier liquid or solvent could be applied as a coating, or as a plurality of coating layers. The coating, specifically the release-blocking polymer, could be cured by heating and/or by the use of a solvent.

All patents and patent applications and publications cited herein are incorporated by reference in their entirety. The above description of illustrated embodiments of the invention is not intended to be exhaustive or to limit the invention to the precise form disclosed. While specific embodiments of, and examples for, the invention are described herein for illustrative purposes, various equivalent modifications are possible within the scope of the invention, as those skilled in the relevant art will recognize. Aspects of the invention can be modified, if necessary, to employ the process, apparatuses and concepts of the various patents and applications described above to provide yet further embodiments of the invention. These and other changes can be made to the invention in light of the above detailed description. In general, in the following claims, the terms used should not be construed to limit the invention to the specific embodiments disclosed in the specification and the claims, but should be construed to include all dosage forms that operate under the claims. Accordingly, the invention is not limited by the disclosure, but instead the scope of the invention is to be determined entirely by the following claims.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A diffusion controlled dosage form having at least one unit providing a diffusion controlled release of Active Pharmaceutical Ingredient, the unit comprising:
   a powder comprising particles of release blocking-polymer and particles of release-regulating polymer, wherein the release-blocking polymer is substantially insoluble in water but is soluble at room temperature in a solvent other than water;
   a printed core comprising the powder and at least one Active Pharmaceutical Ingredient, wherein the powder particles are bound to each other by Active Pharmaceutical Ingredient; and
   a printed shell that surrounds the core, the shell comprising the powder, wherein the powder particles are bound to each other;
   wherein the unit provides a diffusion controlled release of Active Pharmaceutical Ingredient upon exposure to water or bodily fluid;
   the core has a core ratio of release-blocking polymer to release-regulating polymer in the core, the shell has a shell ratio of release-blocking polymer to release-regulating polymer in the shell, and the core ratio is substantially the same as the shell ratio; and
   the core comprises the same release-blocking polymer and the same release-regulating polymer as contained in the shell.

2. The dosage form of claim 1 wherein at least some of the release-regulating polymer in the shell exists in the form of individual particles, which may touch other particles.

3. The dosage form of claim 1 wherein at least some of the release-regulating polymer in the shell exists in the form of tortuous continuous paths, which may include wider parts and narrower parts.

4. The dosage form of claim 1 wherein at least some of the release-regulating polymer in the shell exists in the form of a three-dimensionally interconnected network.

5. The dosage form of claim 1 wherein the shell is substantially free of microscopic defects.

6. The dosage form of claim 1 wherein the shell has a thickness of at least 100 microns.

7. The dosage form of claim 1 wherein the shell has a thickness of approximately 800 microns.

8. The dosage form of claim 1 wherein at least some of the release-regulating polymer in the shell exists in the form of individual particles having an average particle size dimension, and the shell has a thickness of at least 3 times the average particle size dimension.

9. The dosage form of claim 1 wherein the release-blocking polymer and the release-regulating polymer are present in the shell in a proportion that is determined by a desired time scale of a release profile of the Active Pharmaceutical Ingredient from the dosage form.

10. The dosage form of claim 1 wherein the release-regulating polymer in the shell is in the range of 20% to 60% by volume of the combined total of release-regulating polymer and release-blocking polymer in the shell.

11. The dosage form of claim 1 wherein the release-blocking polymer is substantially unaffected by body fluids.

12. The dosage form of claim 1 wherein the release-blocking polymer is substantially impermeable to water.

13. The dosage form of claim 1 wherein the release-blocking polymer is hydrophobic.

14. The dosage form of claim 1 wherein the release-blocking polymer has at least one component that is soluble in at least one non-aqueous solvent.

15. The dosage form of claim 14 wherein the release-blocking polymer has at least one component that is soluble in ethanol.

16. The dosage form of claim 1 wherein the release-blocking polymer is selected from the group consisting of: a mixture of approximately 80% polyvinyl acetate;
   approximately 19% poylvinyl pyrrolidone; and less than approximately 1% of sodium lauryl sulfate and silica, other polyvinyl acetates, ethyl celluloses, and poly(ethyl acrylate, methyl methacrylate) trimethylammonioethyl methacrylate chloride.

17. The dosage form of claim 1 wherein the release-blocking polymer has at least one component that has a glass transition temperature in an unplasticized state that is less than a temperature that the Active Pharmaceutical Ingredient suffers thermal damage.

18. The dosage form of claim 1 wherein the release-blocking polymer has at least one component that has a glass transition temperature in a plasticized state that is less than a temperature that the Active Pharmaceutical Ingredient suffers thermal damage.

19. The dosage form of claim 1 wherein the release-regulating polymer, upon exposure to water, allows diffusion of aqueous solutions therethrough.

20. The dosage form of claim 1 wherein the release-regulating polymer is capable of forming a gel upon exposure to water.

21. The dosage form of claim 1 wherein the release-regulating polymer absorbs water in a manner which is approximately unaffected by the pH of the water.

22. The dosage form of claim 1 wherein the release-regulating polymer is hydrophilic.

23. The dosage form of claim 1 wherein the release-regulating polymer degrades or dissolves at least slightly upon exposure to body fluids.

24. The dosage form of claim 1 wherein the release-regulating polymer is selected from the group consisting of: hydroxypropyl methylcellulose, hydroxypropyl cellulose, methyl cellulose, carboxymethyl cellulose, polyvinyl alcohol, polyvinyl pyrrolidone, acrylate-methacrylate copolymers, polyethylene glycols, xanthan gum, gellan gum, locust bean gum, guar gum, tragacanth, and sodium alginate.

25. The dosage form of claim 1 wherein the shell has a uniform shell wall thickness.

26. The dosage form of claim 1 wherein the shell has a variable shell wall thickness.

27. The dosage form of claim 1 wherein the shell contains non-pharmaceutical materials.

28. The dosage form of claim 1 wherein the dosage form is a three-dimensionally printed dosage form having dimensional increments of a drop-to-drop-spacing and a line-to-line spacing and a powder layer thickness, and wherein the shell has a thickness of at least one drop-to-drop-spacing or one line-to-line spacing or one powder layer thickness.

29. The dosage form of claim 1 wherein the dosage form is a three-dimensionally printed dosage form has dimensional increments of a drop-to-drop-spacing and a line-to-line spacing and a powder layer thickness, and wherein the shell has a thickness of at least two drop-to-drop-spacings or two line-to-line spacings or two powder layer thicknesses.

30. The dosage form of claim 1 wherein the shell further includes a plasticizer.

31. The dosage form of claim 30 wherein the plasticizer and the release-blocking polymer are soluble in the same solvent.

32. The dosage form of claim 30 wherein the plasticizer is soluble in ethanol.

33. The dosage form of claim 30 wherein the plasticizer is selected from the group consisting of: triethyl citrate, triacetin, diethyl phthalate, acetyltriethyl citrate, acetyltributyl citrate, carboxylic acid esters, and phosphoric acid esters.

34. The dosage form of claim 30 wherein the plasticizer is present in the shell in the form of micelles dispersed in the release-blocking polymer.

35. The dosage form of claim 1 wherein the core includes unbound powder particles.

36. The dosage form of claim 1 wherein at least a portion of the core further includes a core binder substance.

37. The dosage form of claim 1 wherein, in the core, particles of the release-regulating polymer comprise API absorbed within them.

38. The dosage form of claim 1 wherein the core contains more Active Pharmaceutical Ingredient than can be contained in solution at body temperature in a volume of water equal to the void volume in the core.

39. The dosage form of claim 1 wherein the core contains less than or equal to the amount of Active Pharmaceutical Ingredient that can be contained in solution at body temperature in a volume of water equal to the void volume in the core.

40. The dosage form of claim 1 wherein the core contains less than or approximately equal to 0.34 milligrams of Active Pharmaceutical Ingredient per cubic millimeter of core region.

41. The dosage form of claim 1 wherein the Active Pharmaceutical Ingredient is water-soluble.

42. The dosage form of claim 1 wherein the Active Pharmaceutical Ingredient comprises at least one substance from the group consisting of pseudoephedrine hydrochloride, metoprolol, d-chlorpheniramine maleate, chlorpheniramine maleate, diphenhydramine hydrochloride, caffeine, d-brompheniramine maleate, brompheniramine maleate, aminophylline, and orphenadrine citrate.

43. The dosage form of claim 1 wherein the core comprises a central region comprising Active Pharmaceutical Ingredient, and comprises a buffer region, surrounding the central region, wherein the buffer region has at least some porosity and contains substantially no Active Pharmaceutical Ingredient.

44. The dosage form of claim 43 wherein the buffer region is sized so as to provide a desired delay time in a release of the Active Pharmaceutical Ingredient from the dosage form.

45. The dosage form of claim 43 wherein the buffer region is sized so as to prevent an initial burst release of the Active Pharmaceutical Ingredient.

46. The dosage form of claim 43 wherein the buffer region has a thickness of at least 200 micrometers.

47. The dosage form of claim 43 wherein the buffer region comprises the same release-blocking polymer and the same release-regulating polymer as are contained in the shell, and wherein the buffer region has a buffer region ratio of release-blocking polymer to release-regulating polymer in the buffer region and the shell has a shell ratio of release-blocking polymer to release-regulating polymer in the shell, and the buffer region ratio is substantially the same as the shell ratio.

48. The dosage form of claim 43 wherein the dosage form is a three-dimensionally printed dosage form having dimensional increments of a drop-to-drop-spacing and a line-to-line spacing and a powder layer thickness, and wherein the buffer region has a thickness of at least one drop-to-drop-spacing or one line-to-line spacing or one powder layer thickness.

49. The dosage form of claim 1 wherein the unit has a rectangular prismatic shape.

50. The dosage form of claim 1 wherein the unit has a cylindrical shape.

51. The dosage form of claim 1, further comprising at least one additional unit.

52. The dosage form of claim 51 wherein the additional unit or units are joined to the unit by a joining structure that comprises an inter-unit binding substance.

53. The dosage form of claim 52 wherein the inter-unit binding substance is soluble in water.

54. The dosage form of claim 52 wherein the inter-unit binding substance is soluble in aqueous solutions of a specified pH.

55. The dosage form of claim 51 wherein the additional unit or units are substantially identical to the first unit.

56. The dosage form of claim 51 wherein at least one additional unit differs from the first unit.

57. The dosage form of claim 51 wherein at least one additional unit does not comprise a shell.

58. The dosage form of claim 1, further including a capsule that encloses the unit or units.

59. The dosage form of claim 1 wherein the core has a void fraction of greater than 20%.

60. The dosage form of claim 1 wherein the unit or the dosage form has a void fraction less than 5%.

61. A method of forming a dosage form according to claim 1, comprising three-dimensionally printing a core and a shell each comprising a release-blocking polymer and particles of a release-regulating polymer.

62. The dosage form of claim 1 wherein the dosage form is manufactured by methods that include three-dimensional printing.

* * * * *